United States Patent [19]
Bouchard et al.

[11] Patent Number: 5,556,877
[45] Date of Patent: Sep. 17, 1996

[54] TAXOIDS, THEIR PREPARATION AND THE PHARMACEUTICAL COMPOSITIONS WHICH CONTAIN THEM

[75] Inventors: Hervé Bouchard, Ivry Sur Seine; Jean-Dominique Bourzat, Vincennes; Alain Commerçon, Vitry-Sur-Seine; Jean-Pierre Pulicani, Antony, all of France

[73] Assignee: Rhone-Poulenc Rorer S.A., Antony, France

[21] Appl. No.: 204,128

[22] Filed: Mar. 2, 1994

[30] Foreign Application Priority Data

Mar. 2, 1993 [FR] France .................................. 93 02370

[51] Int. Cl.⁶ ...................... A61K 31/335; C07D 305/14
[52] U.S. Cl. .................. 514/449; 514/365; 514/372; 514/444; 514/471; 548/146; 549/60; 549/472; 549/473; 549/510; 549/511
[58] Field of Search ...................... 549/510, 511; 514/449

[56] References Cited

U.S. PATENT DOCUMENTS 5,254,703  10/1993  Holton .................................... 549/510
5,430,160   7/1995  Holton .................................... 549/510

Primary Examiner—Ba Kim Trinh
Attorney, Agent, or Firm—Finnegan, Henderson, Farabow, Garrett & Dunner, L.L.P.

[57] ABSTRACT

This invention relates to taxoids of general formula (I), their preparation and the pharmaceutical compositions which contain them. The products of general formula (I) have notable antitumoral properties. In the general formula (I), Ar represents an aryl radical, R represents a hydrogen atom or an acetyl or alkoxyacetyl radical, $R_1$ represents a benzoyl radical or a radical $R_2$—O—CO— in which $R_2$ represents an alkyl, alkenyl, cycloalkyl, cycloalkenyl, bicycloalkyl, phenyl or heterocyclyl radical, and $R_3$ represents an alkyl, alkenyl, cycloalkyl, cycloalkenyl, bicycloalkyl, optionally substituted aryl (with the exception of unsubstituted phenyl) or heterocyclyl radical.

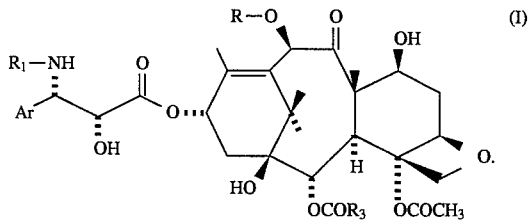

6 Claims, No Drawings

TAXOIDS, THEIR PREPARATION AND THE PHARMACEUTICAL COMPOSITIONS WHICH CONTAIN THEM

DESCRIPTION OF THE INVENTION

The present invention relates to new taxoids of general formula:

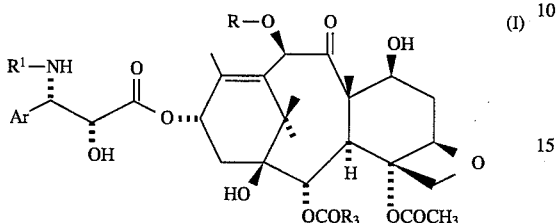

to their preparation and to the pharmaceutical compositions which contain them.

In the general formula (I),

Ar represents an aryl radical or a heterocylic radical,

R represents a hydrogen atom or an acetyl or alkoxyacetyl radical, $R_1$ represents a benzoyl radical or a radical $R_2$—O—CO— in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals optionally being substituted by one or a number of substituents chosen from halogen atoms and hydroxyl, alkyloxy, containing 1 to 4 carbon atoms, dialkylamino, in which each alkyl part contains 1 to 4 carbon atoms, piperidino, morpholino, 1-piperazinyl (optionally substituted in the 4-position by an alkyl radical containing 1 to 4 carbon atoms or by a phenylalkyl radical in which the alkyl part contains 1 to 4 carbon atoms), cycloalkyl, containing 3 to 6 carbon atoms, cycloalkenyl, containing 4 to 6 carbon atoms, phenyl, cyano, carboxyl or alkyloxycarbonyl, in which the alkyl part contains 1 to 4 carbon atoms, radicals, or a phenyl radical optionally substituted by one or a number of atoms or radicals chosen from halogen atoms and alkyl, containing 1 to 4 carbon atoms, or alkyloxy, containing 1 to 4 carbon atoms, radicals, or a saturated or unsaturated heterocyclyl radical containing 4 to 6 members and optionally substituted by one or a number of alkyl radicals containing 1 to 4 carbon atoms, and $R_3$ represents a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals optionally being substituted by one or a number of substituents chosen from halogen atoms and hydroxyl, alkyloxy, containing 1 to 4 carbon atoms, dialkylamino, in which each alkyl part contains 1 to 4 carbon atoms, piperidino, morpholino, 1-piperazinyl (optionally substituted in the 4-position by an alkyl radical containing 1 to 4 carbon atoms or by a phenylalkyl radical in which the alkyl part contains 1 to 4 carbon atoms), cycloalkyl, containing 3 to 6 carbon atoms, cycloalkenyl, containing 4 to 6 carbon atoms or phenyl, optionally substituted by cyano, carboxyl or alkyloxycarbonyl, in which the alkyl part contains 1 to 4 carbon atoms, radicals, or an aryl radical optionally substituted by one or a number of atoms or radicals chosen from halogen atoms and alkyl, containing 1 to 4 carbon atoms, or alkyloxy, containing 1 to 4 carbon atoms, radicals, it being understood that $R_3$ cannot represent an unsubstituted phenyl radical, or a saturated or unsaturated heterocyclyl radical containing 4 to 6 members and optionally substituted by one or a number of halogen atoms, alkyl radicals containing 1 to 4 carbon atoms or alkoxy radicals of 1 to 4 carbon atoms, it being understood that the cycloalkyl, cycloalkenyl or bicycloalkyl radicals can optionally be substituted by one or a number of alkyl radicals containing 1 to 4 carbon atoms.

The aryl radicals represented by Ar and $R_3$ are preferably phenyl or α- or β-naphthyl radicals optionally substituted by one or a number of atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals, and that the $R_3$ radical cannot represent an unsubstituted phenyl radical.

The heterocyclic radicals represented by Ar and $r_3$ are preferably aromatic heterocyclic radicals having 5 members and containing one or a number of atoms, which are identical or different, chosen from nitrogen, oxygen or sulphur atoms, optionally substituted by one or a number of substituents, which are identical or different, chosen from halogen atoms (fluorine, chlorine, bromine, iodine) and alkyl, containing 1 to 4 carbon atoms, aryl, containing 6 to 10 carbon atoms, alkoxy, containing 1 to 4 carbon atoms, aryloxy, containing 6 to 10 carbon atoms, amino, alkylamino, containing 1 to 4 carbon atoms, dialkylamino, in which each alkyl part contains 1 to 4 carbon atoms, acylamino, in which the acyl part contains 1 to 4 carbon atoms, alkoxycarbonylamino, containing 1 to 4 carbon atoms, acyl, containing 1 to 4 carbon atoms, arylcarbonyl, in which the aryl part contains 6 to 10 carbon atoms, cyano nitrotrifluoromethyl, carboxyl, carbamoyl, alkylcarbamoyl, in which the alkyl part contains 1 to 4 carbon atoms, dialkylcarbamoyl, in which each alkyl part contains 1 to 4 carbon atoms, or alkoxycarbonyl, in which the alkoxy part contains 1 to 4 carbon atoms, radicals.

More particularly, Ar represents a phenyl, 2- or 3-thienyl or 2- or 3-furyl or 2-, 4- or 5- thiazolyl radical, optionally substituted by one or a number of atoms or radicals, which are identical or different, chosen from halogen atoms and alkyl, alkoxy, amino, alkylamino, dialkylamino, acylamino, alkoxycarbonylamino and trifluoromethyl radicals and $R_3$ represents a phenyl radical substituted by one or a number of atoms or radicals, which are identical or different, chosen from halogen atoms and alkyl, alkoxy, amino, alkylamino, dialkylamino, acylamino, alkoxycarbonylamino, nitro and trifluoromethyl radicals, or a 2- or 3- thienyl or 2- or 3-furyl radical optionally substituted by one or more halogen atoms or alkyl, alkoxy, amino, aklylamino, dialkylamino, acylamino, alkoxycarbonylamino or trifluoromethyl radicals.

More particularly still, Ar represents a phenyl radical optionally substituted by a chlorine or fluorine atom or by an alkyl (methyl), alkoxy (methoxy), dialkylamino (dimethylamino), acylamino (acetylamino), alkoxycarbonylamino (tertbutoxycarbonylamino), carboxyl, or carbamoyl, or 2- or 3-thienyl, 2- or 3-furyl, or 2-, 4- or 5-thiazolyl radical and $R_3$ represents a phenyl radical. substituted by one or a number of halogen atoms or by an alkyl (ethyl, tert-butyl), alkoxy (methoxy), nitro or trifluoromethyl radical.

Of even more particular interest are the products of general formula (I) in which Ar represents a phenyl radical and $R_1$ represents a benzoyl or tert-butoxycarbonyl radical and $R_3$ represents a 2-fluorophenyl, 3-fluorophenyl, 4-fluorophenyl, pentafluorophenyl, 4-ethylphenyl, 4-(tert-butyl)phenyl, 3-nitrophenyl, 4-nitrophenyl or trifluoromethyl radical.

According to the invention, the new taxoids of general formula (I) can be obtained by esterification of a product of general formula:

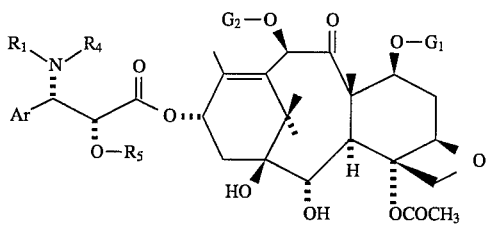

(II)

in which Ar and $R_1$ are defined as above and either $R_4$ represents a hydrogen atom and $R_5$ represents a protective group of the hydroxyl functional group or else $R_4$ and $R_5$ together form a saturated 5- or 6-membered heterocycle, $G_1$ represents a protective group of the hydroxyl functional group and $G_2$ represents an acetyl radical or a protective group of the hydroxyl functional group, by means of an acid of general formula:

$$R_3—CO—OH \quad (III)$$

in which $R_3$ is defined as above, or of an activated derivative of this acid, to obtain a product of general formula:

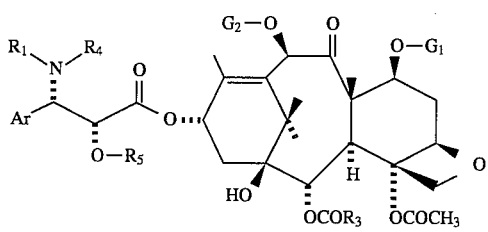

(IV)

in which Ar, $R_1$, $R_3$, $R_4$, $R_5$, $G_1$ and $G_2$ are defined as above, the replacement of the protective groups $R_5$, when $R_4$ represents a hydrogen atom, or else $R_4$ and $R_5$, when $R_4$ and $R_5$ together form a saturated 5- or 6-membered heterocycle, $G_1$ and optionally $G_2$ of which by hydrogen atoms leads to the product of general formula (I), optionally passing, depending on the meanings of $R_1$, $R_4$ and $R_5$, through a product of general formula:

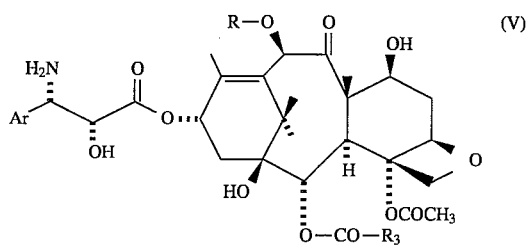

(V)

in which R is defined as above, which is acylated by means of benzoyl chloride or of a product of general formula:

$$R_2—O—CO—X \quad (VI)$$

in which $R_2$ is defined as above and X represents a halogen atom (fluorine, chlorine) or a —O—$R_2$ or —O—CO—O—$R_2$ residue.

When $R_4$ represents a hydrogen atom, $R_5$ preferably represents a methoxymethyl, 1-ethoxyethyl, benzyloxymethyl, trimethylsilyl, triethylsilyl, (β-trimethylsilylethoxy)methyl or tetrahydropyranyl radical. When $R_4$ and $R_5$ together form a heterocycle, the latter is preferably an oxazolidine ring optionally monosubstituted or gem-disubstituted in the 2-position.

When $G_1$ and $G_2$ represent a protective group of the hydroxyl functional group, these groups are generally different. $G_1$ preferably represents a trialkylsilyl, dialkylarylsilyl, alkyldiarylsilyl or triarylsilyl radical in which the alkyl parts contain 1 to 4 carbon atoms and the aryl parts are preferably phenyl radicals and $G_2$ represents an alkoxyacetyl radical such as methoxyacetyl.

Esterification of the product of general formula (II) can be carried out by reacting the acid of general formula (III), preferably in the halide form, such as the chloride, with the product of general formula (II) which has been metallated beforehand. The metallation is generally carried out by means of an alkali metal alkylide such as butyllithium, the reaction being carried out in an inert organic solvent such as an ether such as tetrahydrofuran at a temperature below −50° C. and preferably in the region of −78° C. Esterification is generally carried out by carrying out the reaction at the same temperature in the same solvent.

Depending on the nature of the protective groups of the product of general formula (IV), their replacement by hydrogen atoms can be carried out in the following way:

1) when $R_4$ represents a hydrogen atom, $R_5$ is defined as above and $G_1$ represents a silylated radical and $G_2$ represents an acetyl radical, the replacement of the protective groups by hydrogen atoms can be carried out by treating the product of general formula (IV) with an inorganic acid (hydrochloric acid, sulphuric acid, hydrofluoric acid) or organic acid (formic acid, acetic acid, methanesulphonic acid, trifluoromethanesulphonic acid, p-toluenesulphonic acid), used alone or as a mixture, the reaction being carried out in an organic solvent chosen from alcohols, ethers, esters, aliphatic hydrocarbons, halogenated aliphatic hydrocarbons, aromatic hydrocarbons or nitriles at a temperature between −10° and 60° C.

2) when $R_4$ and $R_5$ together form a saturated 5- or 6-membered heterocycle and more particularly an oxazolidine ring of general formula:

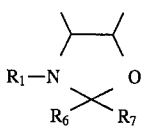 (VII)

in which $R_1$ is defined as above, $R_6$ and $R_7$, which are identical or different, represent a hydrogen atom or an alkyl radical containing 1 to 4 carbon atoms, or an aralkyl radical in which the alkyl part contains 1 to 4 carbon atoms and the aryl part preferably represents a phenyl radical optionally substituted by one or a number of alkoxy radicals containing 1 to 4 carbon atoms, or an aryl radical preferably representing a phenyl radical optionally substituted by one or a number of alkoxy radicals containing 1 to 4 carbon atoms, or else $R_6$ represents an alkoxy radical containing 1 to 4 carbon atoms or a trihalomethyl radical such as trichloromethyl or a phenyl radical substituted by a trihalomethyl radical such as trichloromethyl and $R_7$ represents a hydrogen atom, or else $R_6$ and $R_7$ form, together with the carbon atom to which they are bonded, a ring having 4 to 7 members, $G_1$ represents a silylated radical and $G_2$ represents an acetyl radical, the replacement of the protective groups by hydrogen atoms can be carried out, depending on the meanings of $R_1$, $R_6$ and $R_7$, in the following way:

a) when $R_1$ represents a t-butoxycarbonyl radical, $R_6$ and $R_7$, which are identical or different, represent an alkyl radical or an aralkyl (benzyl) or aryl (phenyl) radical, or else $R_6$ represents a trihalomethyl radical or a phenyl radical substituted by a trihalomethyl radical and $R_7$ represents a hydrogen atom, or else $R_6$ and $R_7$ together form a ring having 4 to 7 members, the treatment of a product of general formula (IV) with an inorganic or organic acid, optionally in an organic solvent such as an alcohol, leads to a product of general formula (V) which is acylated by means of a product of general formula (VI). The product of general formula (IV) is preferably treated with formic acid at a temperature in the region of 20° C. The acylation of the product of general formula (V) by means of a product of general formula (VI) is preferably carried out in an inert organic solvent chosen from esters such as ethyl acetate, isopropyl acetate or n-butyl acetate and halogenated aliphatic hydrocarbons such as dichloromethane or 1,2-dichloroethane in the presence of an inorganic base such as sodium bicarbonate or an organic base such as triethylamine. The reaction is carried out at a temperature between 0° and 50° C., preferably in the region of 20° C.

b) when $R_1$ represents a benzoyl radical or a radical $R_2$—O—CO— in which $R_2$ is defined as above, $R_6$ represents a hydrogen atom or an alkoxy radical containing 1 to 4 carbon atoms or a phenyl radical substituted by one or a number of alkoxy radicals containing 1 to 4 carbon atoms and $R_7$ represents a hydrogen atom, the replacement of the protective groups by hydrogen atoms is carried out in the presence of an inorganic acid (hydrochloric acid, sulphuric acid) or organic acid (acetic acid, methanesulphonic acid, trifluoromethanesulphonic acid, p-toluenesulphonic acid), used alone or as a mixture, the reaction being carried out in an organic solvent chosen from alcohols, ethers, esters, aliphatic hydrocarbons, halogenated aliphatic hydrocarbons and aromatic hydrocarbons at a temperature between −10° and 60° C., preferably between 15° and 30° C. The acid can be used in a catalytic or stoichiometric amount.

3) when $G_1$ represents a silylated radical, $G_2$ represents an alkoxyacetyl radical and $R_4$ and $R_5$ are defined as in point 1) above, replacement of the protective groups $G_1$ and $R_5$ by hydrogen atoms is first carried out, the reaction being carried out under the acidic conditions described in point 1 above, and then the protective group $G_2$ is optionally replaced by a hydrogen atom by treatment in alkaline medium under conditions which do not affect the remainder of the molecule. The alkaline treatment is generally carried out by reacting with ammonia in aqueous/alcoholic medium at a temperature in the region of 20° C. or by the action of a zinc halide, e.g. zinc bromide or iodide, in methanol at a temperature of about 20° C.

4) When $G_1$ represents a silylated radical, $G_2$ represents an alkoxyacetyl radical and $R_4$ and $R_5$ are defined as in point 2-a) above, replacement of the protective group $G_1$ is carried out first by a treatment in acidic medium under conditions which do not affect the remainder of the molecule, for example by means of hydrochloric acid diluted in an alcohol such as ethanol at a temperature in the region of 0° C., then the protective group $G_2$ is optionally replaced by hydrogen atom under the conditions described in point 3) above, and then the product of general formula (V) obtained is treated under the deprotection and acylation conditions described in point 2-a) above.

5) when $G_1$ represents a silylated radical, $G_2$ represents an alkoxyacetyl radical and $R_4$ and $R_5$ are defined as in point 2-b) above, replacement of the protective group $G_1$ is carried out first by a treatment in acidic medium under conditions which do not affect the remainder of the molecule, for example by means of hydrochloric acid diluted in an alcohol such as ethanol at a temperature in the region of 0° C., the protective group $G_2$ is then optionally replaced by a hydrogen atom under the conditions described in point 3) above, and then the product obtained is treated under the conditions described in point 2-b) above.

According to the invention, the products of general formula (II) can be obtained by electrolytic reduction of a product of general formula:

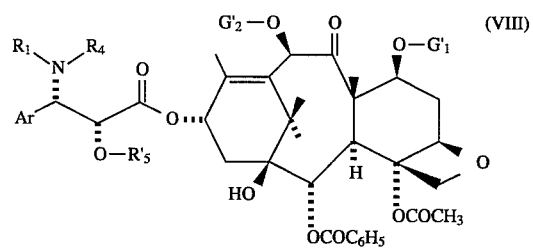 (VIII)

in which Ar, $R_1$ and $R_4$ are defined as above, $R'_5$ represents a hydrogen atom or a protective group of the hydroxyl functional group, $R_4$ representing a hydrogen atom, $G'_1$ represents a hydrogen atom or a protective group of the hydroxyl functional group and $G'_2$ represents a hydrogen atom, an acetyl radical or a protective group of the hydroxyl functional group, according to the following scheme:

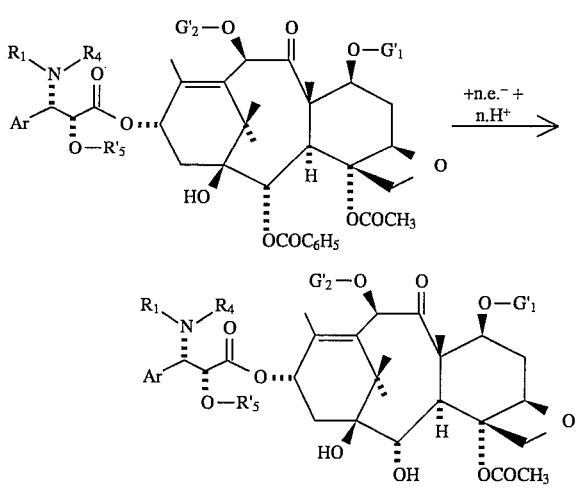

it being understood that, when n is equal to 2, the cleavage product is benzaldehyde and, when n is equal to 4, the cleavage product is benzyl alcohol, optionally followed by protection of the hydroxyl functional groups defined by —OR'$_5$, —O—G'$_1$ and —O—G'$_2$, to obtain the product of general formula (II).

Electrolytic reduction starting from the product of general formula (VIII) is carried out in an electrolyzer containing a support catholyte in which the product of general formula (VIII) is dissolved at a concentration of between 0.1 g/l and saturation of the solution in the product of general formula (VIII).

The reduction is preferentially carried out in a diaphragm electrolyzer.

According to an embodiment of the process according to the invention, the electrolytic reduction is carried out in an electrolyzer containing a cathode, a cathode compartment, a separating diaphragm, an anode compartment and an anode, the characteristics of which are the following:

a) the cathode consists of a mercury sheet,
b) the cathode compartment contains the catholyte, which consists of a solution of the product of general formula (VIII) in an organic medium,
c) the separating diaphragm consists of a porous material such as a plate, a sleeve tube or a candle made of sintered glass or porcelain or an ion-exchange membrane, preferably a cation-exchange membrane,
d) the anode compartment contains the anolyte, preferably consisting of the same solvent or mixture of solvents and the same support electrolyte as that which is used in the cathode compartment,
e) the anode consists of an electrically-conductive material, the nature of which is not essential to the implementation of the process.

The anode generally consists of an electrically-conductive material which cannot be attacked under the electrolysis conditions, such as, for example, polished platinum, in the bulk form or on a conductive support, graphite or vitreous carbon.

The support electrolyte consists of a quaternary ammonium salt such as tetramethylammonium acetate, tetraethylammonium acetate or tetraethylammonium tetrafluoroborate, or their mixtures, which is soluble in the solvent or the mixture of solvents.

Solvents are generally used which easily dissolve the products of general formula (II) and (VIII) and which have little resistance such as alcohols, such as methanol, nitriles, such as acetonitrile, or amides, such as dimethylformamide.

The pH must be compatible with the stability of the substrate. The medium must be buffered by adding a weak acid such as acetic acid to the solution of the quaternary ammonium salt.

According to a preferred embodiment of the process, the anode, the cathode and the separating diaphragm are in parallel horizontal planes, the cathode consisting of a mercury sheet.

The temperature of the electrolysis bath is generally between 0° and 30° C. It is preferably maintained below 20° C.

Electrolysis is carried out at a controlled potential which can be between −1.85 and −2.10 volts with respect to a saturated calomel reference electrode.

It is necessary to deaerate the solution by sparging with an inert gas such as argon for about 10 minutes before beginning electrolysis, the inert atmosphere being maintained throughout the duration of the electrolysis.

In order to obtain a product of general formula (II) in which G$_1$, G$_2$ and R$_5$ each represent a protective group of the hydroxyl functional group, the hydroxyl functional groups of the product of general formula (VIII) defined by —O—G'$_1$ and —O—R'$_5$ are protected first before the hydroxyl functional group defined by —O—G'$_2$ is protected.

The protection of the hydroxyl functional groups of the product of general formula (VIII) defined by —O—G'$_1$ and —O—R'$_5$ in the silylated ether form is preferably generally carried out by reacting with a halosilane of general formula:

in which X represents a halogen atom and the R$_8$ radicals, which are identical or different, represent a trialkylsilyl, dialkylarylsilyl, alkyldiarylsilyl or triarylsilyl radical in which the alkyl parts contain 1 to 4 carbon atoms and the aryl parts are preferably phenyl radicals.

The reaction of the product of general formula (IX) with the product of general formula (VIII) in which G'$_1$, G'$_2$ and R'$_5$ each represent a hydrogen atom 2 5 is generally carried out in a basic organic solvent such as pyridine or in an inert organic solvent such as dichloromethane or chloroform in the presence of an organic base such as triethylamine or Hünig's base or pyridine at a temperature in the region of 20° C.

The protection of the hydroxyl functional group of the product of general formula (VIII) defined by —O—G'$_2$ in the form of an alkoxyacetyl radical is preferably carried out by reacting with an acid halide of general formula:

in which R$_9$ represents an alkyl radical containing 1 to 4 carbon atoms and Y represents a halogen atom, the reaction being carried out in a basic organic solvent such as pyridine at a temperature in the region of 20° C.

According to the invention, the products of general formula (II) can also be obtained by esterification of a product of general formula:

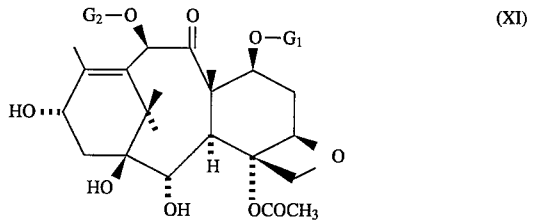

in which G$_1$ and G$_2$ are defined as above, by means of an acid of general formula:

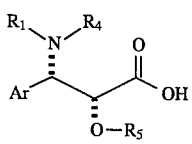

(XII)

in which Ar, $R_1$, $R_4$ and $R_5$ are defined as above, or of a derivative of this acid such as a halide or the anhydride or a mixed anhydride, the reaction being carried out in an organic solvent such as toluene in the presence of an activating agent such as an aminopyridine such as 4-dimethylaminopyridine or 4-pyrrolidinopyridine and optionally of a condensation agent such as an imide such as dicyclohexylcarbodiimide at a temperature between 0° and 90° C.

The product of general formula (XI) can be obtained by electrolytic reduction of a product of general formula:

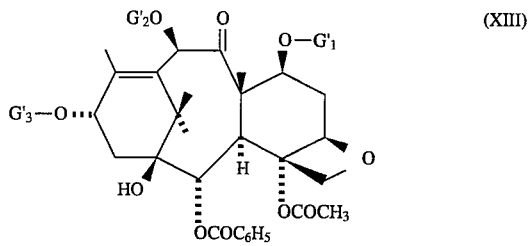

(XIII)

in which $G'_1$ and $G'_2$ are defined as above and $G'_3$ represents a hydrogen atom or a protective group of the hydroxyl functional group identical to $G'_1$, the reaction being carried out under conditions identical to those used for the electrolytic reduction of a product of general formula (VIII).

Depending on the circumstances, it is necessary to selectively replace the protective group $G'_3$ by a hydrogen atom or to selectively protect the hydroxyl functional groups in the 7- and 10-positions before carrying out the esterification.

EXAMPLES

The following examples illustrate the present invention.

EXAMPLE 1

1.1 cm³ of a 1.6M solution of n-butyllithium in hexane are added dropwise, at a temperature of −78° C., to a solution of 1.5 g of 4,10β-diacetoxy-1,2α-dihydroxy- 5β,20-epoxy-9-oxo-7β-triethylsilyloxy-11-taxen-13α-yl (4S,5R)-3-tert-butoxycarbonyl-2,2-dimethyl-4-phenyloxazolidine-5-carboxylate in 16 cm³ of anhydrous tetrahydrofuran, maintained under an argon atmosphere. On completion of the addition, the reaction mixture is stirred for 20 minutes at a temperature in the region of −78° C. and then 0.3 cm³ of 3-fluorobenzoyl chloride is added dropwise at the same temperature. The reaction mixture is kept stirring at −78° C. for 3 hours, the temperature is then allowed to rise to the region of 0° C. and then 5 cm³ of a saturated aqueous ammonium chloride solution are added. The organic phase is separated by settling, washed with 2 times 10 cm³ of distilled water, dried over magnesium sulphate, filtered and then concentrated to dryness under reduced pressure (2.7 kPa) at 40° C. There is obtained 1.7 g of a white foam which is purified by chromatography on 50 g of silica (0.063–0.2 mm) contained in a column with a diameter of 2.5 cm [eluent: dichloromethane/methanol (99/1 by volume)], 3 cm³ fractions being collected. The fractions which contain only the desired product are combined and concentrated to dryness under reduced pressure (2.7 kPa) at a temperature in the region of 40° C. There is thus obtained 0.48 g of 4,10β-diacetoxy-5β, 20-epoxy-2α-(3-fluorobenzoyloxy)-1-hydroxy-9-oxo- 7β-triethylsilyloxy-11-taxen-13α-yl (4S,5R)-3-tert-butoxycarbonyl-2,2-dimethyl-4-phenyloxazolidine-5-carboxylate in the form of a white foam.

A solution of 0.48 g of 4,10β-diacetoxy- 5β, 20-epoxy-2α-(3-fluorobenzoyloxy)-1-hydroxy-9-oxo-7β-triethylsilyloxy- 11-taxen-13α-yl (4S,5R)-3-tert-butoxycarbonyl-2,2-dimethyl-4-phenyloxazolidine-5carboxylate in 4.8 cm³ of formic acid is stirred for 2.5 hours at a temperature in the region of 20° C. and then concentrated to dryness under reduced pressure (0.7 kPa, then 0.07 kPa) at 30° C. The residue is treated with 20 cm³ of dichloromethane and then with 20 cm³ of a saturated aqueous sodium hydrogencarbonate solution. The aqueous phase is separated by settling and reextracted with 20 cm³ of dichloromethane. The organic phases are combined, dried over magnesium sulphate, filtered and then concentrated to dryness under reduced pressure (2.7 kPa) at 40° C. There is obtained 0.33 g of a white foam which is purified by chromatography on 20 g of silica (0.063–0.2 mm) contained in a column with a diameter of 2 cm [eluent: dichloromethane/methanol (98/2 by volume)], 10 cm³ fractions being collected. The fractions which only contain the desired product are combined and concentrated to dryness under reduced pressure (2.7 kPa) at a temperature in the region of 40° C. There is thus obtained 0.091 g of 4,10β-diacetoxy-1,7β-dihydroxy- 5β,20-epoxy-2α-(3-fluorobenzoyloxy)-9-oxo- 11-taxen-13α-yl (2R,3S)-3-amino-2-hydroxy-3-phenylpropionate in the form of a white foam.

2.5 cm³ of a saturated sodium hydrogencarbonate solution and 2.5 cm³ of distilled water and then, in a single step, 0.014 cm³ (14 μl) of benzoyl chloride are added to a solution of 87 mg of 4,10β-diacetoxy-1,7β-dihydroxy-5β, 20-epoxy-2α-( 3-fluorobenzoyloxy)-9-oxo-11-taxen-13α-yl (2R,3S)-3-amino-2-hydroxy-3-phenylpropionate in 2.5 cm³ of ethyl acetate, maintained under an argon atmosphere. The reaction mixture is stirred for 15 minutes at a temperature in the region of 20° C. The aqueous phase is separated by settling and then reextracted with 3 times 3 cm³ of ethyl acetate. The organic phases are combined, dried over magnesium sulphate, filtered and then concentrated to dryness under reduced pressure (2.7 kPa) at 40° C. There are obtained 88 mg of a white foam which is purified by-chromatography on 3 g of silica (0.063–0.2 mm) contained in a column with a diameter of 1 cm [eluent: dichloromethane/methanol (98/2 by volume)], 1.5 cm³ fractions being collected. Fractions 14 to 21 are combined and concentrated to dryness under reduced pressure (0.27 kPa) at 40° C. There are thus obtained 80 mg of 4,10β-diacetoxy-1,7β-dihydroxy- 5β,20-epoxy-2α-(3- fluorobenzoyloxy)-9-oxo-11-taxen-13α-yl (2R, 3S) -3-benzoylamino-2-hydroxy-3-phenylpropionate in the form of a white foam, the characteristics of which are the following:

optimal rotation: $[\alpha]_D^{20}$ =−45° (c=1.0, methanol)
N.M.R. spectrum: (400 MHz, CDCl$_3$, δ in ppm).
1.15 (s, 3H, —CH$_3$ 16 or 17), 1.25 (s, 3H, —CH$_3$ 16 or 17), 1.69 (s, 3H, —CH$_3$ 19), 1.80 (s, 3H, —CH$_3$ 18), 1.89 (mt, 1H, —(CH) —H 6), 1.94 (s, 1H, —OH1), 2.26 (s, 3H, —COCH$_3$ at 10), 2.32 (d, J=9 Hz, 2H, —CH$_2$- 14), 2.37 (s, 3H, —COCH$_3$ at 4), 2.53 (d, J=4 Hz, 1H, —OH 7), 2.55 (mt, 1H, —(CH)—H 6), 3.69 (d, J=5 Hz, 1H, —O H2'), 3,80 (d, J=7 Hz, 1H, -H 3), 4.18 and 4.30 (2d, J=8 Hz, each 1H, —(CH$_2$)— 20), 4.40 (mt, 1H, —H 7), 4.78 (dd, J=5 and 3 Hz, 1H, —H 2'), 4.96 (dd, J=10 and 2 Hz, 1H, —H 5), 5.65 (d, J=7 Hz, 1H, —H −2), 5.77 (dd, J=9.5 and 3 Hz, 1H, —H 3'), 6.21 (t, J −9 Hz, 1H, —H 13), 6.28 (s, 1H, —H 10), 7.00 (d, J=9.5 Hz, 1H, —NHCO—), 7.30 to 7.50 (mt, 7H, —C$_6$H$_5$ at 3', —NHCOC$_6$H$_5$ (—H 4), —OCOC$_6$H$_4$F (—H 4), 7.50 (t, J=7.5 Hz, 2H, —NHCOC$_6$H$_5$ (—H 3 and —H 5) ) , 7.50 (mt, 1H, —OCOC$_6$H$_4$F (—H 5)), 7.63 (D, J=7.5 Hz, 2H, —NHCOC$_6$H$_5$ (—H 2 and —H 6)), 7.81 (broad d, J=9 Hz, 1H, —OCOC$_6$H$_4$F (—H 2)), 7.94 (d, J=7.5 Hz, 1H, —OCOC$_6$H$_4$F (—H 6)).

4,10β-Diacetoxy-1,2α-dihydroxy-5β,20-epoxy-9-oxo-7β-triethylsilyloxy- 11-taxen-13α-yl (4S,5R)-3-tert-butoxycarbonyl-2,2-dimethyl-4-phenyloxazolidine-5carboxylate can be prepared in the following way:

The electrolytic reduction of 4,10β-diacetoxy-1-hydroxy-2α-benzoyloxy-5β,20-epoxy- 9-oxo-7β-triethylsilyloxy-11-taxen-13α-yl (4S,5R)-3-tert-butoxycarbonyl-2,2-dimethyl-4-phenyloxazolidine-5carboxylate is carried out in an electrolysis cell having the following characteristics:

the cell is a 50 cm$^3$ glass tank divided into two compartments by a cation-exchange membrane,
the cathode is a mercury sheet whose working surface area is approximately 12 cm$^2$,
the anode is a platinum grid,
the reference electrode is a saturated calomel electrode.
50 cm$^3$ of a solution containing:

| | |
|---|---|
| 4,10β-diacetoxy-1-hydroxy-2α-benzoyloxy-5β, 20-epoxy-9-oxo-7β-triethylsilyloxy-11-taxen-13α-yl (4S,5R)-3-tert-butoxycarbonyl-2,2-dimethyl-4-phenyloxazolidine-5-carboxylate] | 2.0 g |
| methanol | 50 cm$^3$ |
| tetraethylammonium acetate | q.s. for 0.2 M |
| acetic acid | 0.28 cm$^3$ | are introduced into the cathode compartment.

Approximately 10 cm$^3$ of a solution of the same composition which does not contain the substrate is introduced into the anode compartment.

The cell is immersed in a bath of melting ice. The internal temperature remains in the region of 10° C. After deaerating the solution for 10 minutes by sparging with a stream of argon, the potential of the cathode is fixed at −2.05 volts.

Consumption of H$^+$ ions is compensated for by addition of 0.114 cm$^3$ of acetic acid when 1 faraday per mole of substrate is passed. 0.26 g of tetraethylammonium acetate is also added to the anode compartment at each increase in the electrical resistance.

After passing 960 coulombs, electrolysis is halted. The solvent is evaporated under reduced pressure at a temperature below 35° C. The residue is taken up in 50 cm$^3$ of water. The reaction mixture is extracted with 50 and then 2 times 25 cm$^3$ of ethyl acetate. The organic phase is rinsed with 50 cm$^3$ of an aqueous sodium hydrogencarbonate solution and then dried over magnesium sulphate. After filtration and evaporation of the solvent under reduced pressure at a temperature below 35° C., there is isolated 1.86 g of a white solid which is chromatographed on 100 g of silica (0.063–0.2 mm) contained in a column with a diameter of 24 mm. Elution is carried out with a dichloromethane/methanol (99/1 by volume) mixture, 6 cm$^3$ fractions being collected. Fractions 140 to 220, containing the expected purified product, are combined and concentrated to dryness under reduced pressure (0.27 kPa). There is thus obtained 0.77 g of 4,10β-diacetoxy-1,2α-dihydroxy-5β,20-epoxy-9-oxo-7β-triethylsilyloxy-11-taxen-13α-yl (4S, 5R) -3-tert-butoxycarbonyl -2,2-dimethyl-4-phenyloxazolidine-5-carboxylate in the form of a white foam.

4,10β-Diacetoxy-1-hydroxy-2α-benzoyloxy- 5β,20-epoxy-9-oxo-7β-triethylsilyloxy-11-taxen-13α-yl (4S, 5R)-3-tert-butoxycarbonyl-2,2-dimethyl-4-phenyloxazolidine-5-carboxylate can be prepared under the conditions described in International Application PCT WO 9209589.

EXAMPLE 2

0.65 cm$^3$ of a 1.6M solution of n-butyllithium in hexane is added dropwise at a temperature in the region of −78° C. to a solution of 0.8 g of 4-acetoxy- 1,2α-dihydroxy-5β,20-epoxy-10β-methoxyacetyloxy-9-oxo- 7β-triethylsilyloxy-11-taxen-13α-yl (4S,5R)-3-tert-butoxycarbonyl-2,2-dimethyl-4-phenyloxazolidine-5-carboxylate in 10 cm$^3$ of anhydrous tetrahydrofuran, maintained under an argon atmosphere. On completion of the addition, the reaction mixture is stirred for 30 minutes at a temperature in the region of −78° C. and then 0.157 cm$^3$ of 3-fluorobenzoyl chloride is added dropwise while maintaining the temperature at −78° C. On completion of the addition, the reaction mixture is kept stirring at a temperature in the region of −78° C. for 3 hours, is then reheated to a temperature in the region of 0° C. and 2 cm$^3$ of a saturated aqueous ammonium chloride solution are added. The aqueous phase is separated by settling and reextracted with 3 times 5 cm$^3$ of ethyl acetate. The organic phases are combined, dried over magnesium sulphate, filtered and then concentrated to dryness under reduced pressure (2.7 kPa, then 0.7 kPa) at 40° C. There is obtained 0.91 g of a white foam which is purified by chromatography on 25 g of silica (0.063–0.2 mm) contained in a column with a diameter of 1.5 cm [eluent: dichloromethane/methanol (99/1 by volume)], 3 cm$^3$ fractions being collected. Fractions 35 to 42 are combined and concentrated to dryness under reduced pressure (2.7 kPa) at a temperature in the region of 40° C. There is thus obtained 0.51 g of 4-acetoxy-5β,20-epoxy-2α-( 3-fluorobenzoyloxy)-1-hydroxy-10β-methoxyacetyloxy-9-oxo-7β-triethylsilyloxy-11-taxen- 13α-yl (4S,5R)-3-tert-butoxycarbonyl-2,2-dimethyl-4-phenyloxazolidine-5-carboxylate in the form of a white foam.

0.1 g of 4-acetoxy-5β,20-epoxy-2α-(3-fluorobenzoyloxy)-1-hydroxy-10β-methoxyacetyloxy- 9-oxo-7β-triethylsilyloxy-11-taxen-13α-yl (4S,5R)-3-tert-butoxycarbonyl-2,2-dimethyl-4-phenyloxazolidine-5-carboxylate is added to 2 cm$^3$ of a 0.1N ethanolic hydrochloric acid solution. The solution obtained is stirred for 17 hours at a temperature in the region of 0° C. and then 10 cm$^3$ of dichloromethane and 5 cm$^3$ of a saturated aqueous sodium hydrogencarbonate solution are added. After stirring, the organic phase is separated by settling, dried over magnesium sulphate, filtered and then concentrated to dryness under reduced pressure (2.7 kPa) at 40° C. There are obtained 120 mg of a white foam which is purified by chromatography on 3 g of silica (0.04–0.063 mm) contained in a column with a diameter of 1 cm [eluent: dichloromethane/methanol (99/1 by volume)], 1 cm$^3$ fractions being collected. Fractions 31 to 38 are combined and concentrated to dryness under reduced pressure (2.7 kPa, then 0.07 kPa) at a temperature in the region of 40° C. There are thus obtained 41 mg of 4-acetoxy-1,7β-dihydroxy-5β,20-epoxy- 2α-(3-fluorobenzoyloxy)-10β-methoxyacetyloxy-9-oxo-11-taxen-13α-yl (4S,5R)-3-tert-butoxycarbonyl-2,2-dimethyl-4-phenyloxazolidine-5-carboxylate in the form of a white foam.

0.5 cm$^3$ of a 1M aqueous ammonia solution is added, at a temperature in the region of 20° C., to a solution of 40 mg of 4-acetoxy-1,7β-dihydroxy-5β,20-epoxy-2α-(3-fluorobenzoyloxy)-10β-methoxyacetyloxy-9-oxo-11-taxen-13α-yl (4S,5R)-3-tert-butoxycarbonyl-2,2-dimethyl-4-phenyloxazolidine-5-carboxylate in 1.5 cm$^3$ of methanol. The reaction mixture is stirred for 1 hour at a temperature in the region of 20° C. and then concentrated to dryness under reduced pressure (2.7 kPa, then 0.7 kPa) at 20° C. The residual solid is purified by chromatography on 1.5 g of silica (0.04–0.063 mm) contained in a column with a diameter of 1 cm [eluent: dichloromethane/methanol (98/2 by volume)], 1 cm³ fractions being collected. Fractions 62 to 76 are combined and concentrated to dryness under reduced pressure (2.7 kPa) at 40° C. There are thus obtained 12 mg of 4-acetoxy-5β,20-epoxy-2α-(3-fluorobenzoyloxy)-9-oxo-1,7β,10β-trihydroxy-11-taxen-13α-yl (4S,5R)-3-tert-butoxycarbonyl-2,2-dimethyl-4-phenyloxazolidine-5-carboxylate in the form of a white foam.

A solution of 12 mg of 4-acetoxy-5β,20-epoxy- 2α-(3-fluorobenzoyloxy)-9-oxo-1,7β,10β-trihydroxy-11-taxen-13α-yl (4S,5R)-3-tert-butoxycarbonyl-2,2-dimethyl-4-phenyloxazolidine-5-carboxylate in 0.12 cm³ of formic acid is stirred for 2.5 hours at a temperature in the region of 20° C. and then 10 cm³ of dichloromethane and 0.5 cm³ of a saturated aqueous sodium hydrogencarbonate solution are added. The aqueous phase is separated by settling and reextracted with 1 cm³ of dichloromethane. The organic phases are combined, dried over magnesium sulphate, filtered and concentrated to dryness under reduced pressure (2.7 kPa, then 0.7 kPa) at 40° C. There are thus obtained 10 mg of 4-acetoxy-5β,20-epoxy-2α-(3-fluorobenzoyloxy)-9-oxo-1,7β, 10β-trihydroxy-11-taxen-13α-yl (2R,3S)-3-amino-2-hydroxy-3-phenylpropionate in the form of a white foam.

1.4 mg of sodium hydrogencarbonate and 3.6 mg of di-tert-butyl dicarbonate are added, at a temperature in the region of 20° C., to a solution of 10 mg of 4-acetoxy-5β, 20-epoxy-2α-(3-fluorobenzoyloxy)- 9-oxo-1,7β,10β-trihydroxy-11-taxen-13α-yl (2R,3S)-3-amino-2-hydroxy-3-phenylpropionate in 2 cm³ of tetrahydrofuran, maintained under an argon atmosphere. The reaction mixture is stirred for 8 hours at a temperature in the region of 20° C. and then concentrated to dryness under reduced pressure (2.7 kPa) at a temperature in the region of 30° C. The residual solid is treated with 2 cm³ of dichloromethane and 1 cm³ of distilled water. After stirring, the organic phase is separated by settling, dried over magnesium sulphate, filtered and then concentrated to dryness under reduced pressure (2.7 kPa) at 40° C. There are obtained 21 mg of a white foam which is purified by chromatography on silica gel deposited on a plate (gel thickness 1 mm, 20×20 cm plate) in 10 mg fractions. After using U.V. radiation to localize the region corresponding to the desired adsorbed product, this region is scraped off and the silica collected is washed on sintered glass with 10 times 2 cm³ of dichloromethane and with 5 times 1 cm³ of methanol. The filtrates are combined and concentrated to dryness under reduced pressure (0.27 kPa) at 40° C. There-are thus obtained 4 mg of 4-acetoxy-5β,20-epoxy-2α-(3-fluorobenzoyloxy)-9-oxo- 1,7β,10β-trihydroxy-11-taxen-13α-yl (2R, 3S)-3-tert-butoxycarbonylamino-2-hydroxy- 3-phenylpropionate in the form of a white foam, the characteristics of which are the following:
N.M.R. spectrum: (300 MHz, CDCl₃, δ in ppm).
1.15 (s, 3H, —C$\underline{H}_3$ 16 or 17), 1.25 (s, 3H, —C$\underline{H}_3$ 16 or 17), 1.37 (s, 9H, —C(C$\underline{H}_3$)₃), 1.78 (s, 3H, —C$\underline{H}_3$ 19), 1.82 (s, 1H, —O$\underline{H}$ at 1), 1.87 (s, 3H, —C$\underline{H}_3$ 18), 1.87 (mt, 1H, —(CH)—$\underline{H}$ 6), 2.27 (d, J=9 Hz, 2H, —C$\underline{H}_2$— 14), 2,37 (s, 3H, —COC$\underline{H}_3$), 2.60 (mt, 1H, —(CH)—$\underline{H}$ 6), 3.93 (d, J=7 Hz, 1H, —$\underline{H}$ 3), 4.18 (d, J=8 Hz, 1H, —(CH)—$\underline{H}$ 20), 4.23 (mt, 1H, —$\underline{H}$ 7), 4.32 (d, J=8 Hz, 1H, —(CH)—$\underline{H}$ 20), 4.61 (broad s, 1H, —$\underline{H}$ 2'), 4.96 (broad d, J=10 Hz, 1H, —$\underline{H}$ 5), 5.21 (s, 1H, —$\underline{H}$ 10), 5.33 (broad d, J=10 Hz, 1H —$\underline{H}$ 3'), 5.41 (d, J=10 Hz, 1H, —CON$\underline{H}$—), 5.67 (d, J=7 Hz, 1H, —$\underline{H}$2), 6.21 (t, J=9 Hz, 1H, —$\underline{H}$ 13), 7.30 to 7.50 (mt, 6H, —C₆$\underline{H}_5$ at 3', —OCOC₆H₄F (—$\underline{H}$ 4)), 7.51 (mt, 1H, —OCOC₆H₄F(—$\underline{H}$ 5) ), 7.81 (broad d, J=9 Hz, 1H, —OCOC₆H₄F(—$\underline{H}$ 2)); 7.92 (d, J=7.5 Hz, 1H, —OCOC₆H₄F (—$\underline{H}$ 6)).

4-Acetoxy-1,2α-dihydroxy-5β,20-epoxy-10β-methoxyacetyloxy-9-oxo-7β-triethylsilyloxy- 11-taxen-13α-yl (4S, 5R)-3-tert-butoxycarbonyl-2,2-dimethyl-4-phenyloxazolidine-5-carboxylate can be prepared in the following way:

The electrolytic reduction of 4-acetoxy-1-hydroxy-2α-benzoyloxy-5β,20-epoxy-10β-methoxy-acetyloxy-9-oxo- 7β-triethylsilyloxy-11-taxen-13α-yl (4S,5R)-3-tert-butoxycarbonyl-2,2-dimethyl-4-phenyloxazolidine-5-carboxylate is carried out in an electrolysis cell having the following characteristics:
the cell is a 10 cm³ glass tank divided into 2 compartments by a cation-exchange membrane
the cathode is a mercury sheet whose working surface area is approximately 4 cm³,
the anode is a platinum grid,
the reference electrode is a saturated calomel electrode.

50 cm³ of a solution containing:

| | |
|---|---|
| 4-acetoxy-10β-methoxyacetyloxy-1-hydroxy-2α-benzoyloxy-5β,20-epoxy-9-oxo-7β-triethylsilyloxy-11-taxen-13α-yl (4S,5R)-3-tert-butoxycarbonyl-2,2-dimethyl-4-phenyloxazolidine-5-carboxylate | 0.401 g |
| methanol | 27 cm³ |
| tetraethylammonium tetrafluoroborate | 0.1 M |
| tetrabutylammonium acetate | q.s. for 0.02 M |
| acetic acid | 0.02 M | are introduced into the cathode compartment.

Approximately 10 cm³ of an approximately 0.2M hydrochloric acid solution in methanol are introduced into the anode compartment.

The cell is immersed in a bath of melting ice. The internal temperature remains in the region of 7° C. After deaerating the solution for 10 minutes by sparging with a stream of argon, the potential of the cathode is fixed at −1.9 volts and then at −2.0 volts after passing 150 coulombs.

When the electrical resistance increases, 3.8M methanolic hydrochloric acid solution is added to the anode compartment.

After passing 450 coulombs, electrolysis is halted. The solvent is evaporated under reduced pressure at a temperature below 35° C. The residue is taken up in 25 cm³ of ethyl acetate and then in 25 cm³ of deionized water. The aqueous phase is separated by settling and is extracted with 2 times 12.5 cm³ of ethyl acetate. The organic phase is rinsed with 25 cm³ of sodium phosphate buffer at pH 7.4 and then dried over magnesium sulphate. After filtration and evaporation of the solvent under reduced pressure at a temperature below 35° C., there is isolated 0.355 g of a whitish foam which is chromatographed on 10 g of silica (0.04–0.063 mm) contained in a column with a diameter of 15 mm. Elution is carried out with a dichloromethane/methanol (98/2 by volume) mixture, 15 cm³ fractions being collected. Fractions 21 to 25, containing the expected purified product, are combined and concentrated to dryness under reduced pressure (0.27 kPa) at a temperature below 35° C. There are thus obtained, with a yield of 55%, 195 mg of 4-acetoxy-1,2α-dihydroxy-5β,20-epoxy-10β-methoxyacetyloxy-9-oxo- 7β-triethylsilyloxy-11-taxen-13α-yl (4S,5R)-3-tert-butoxycarbonyl-2,2-dimethyl-4-phenyloxazolidine-5-carboxylate in the form of a white foam.

4-Acetoxy-1-hydroxy-2α-benzoyloxy-5β,20-epoxy-10β-methoxyacetyloxy- 9-oxo-7β-triethylsilyloxy-11-taxen-13α-yl (4S, 5R)-3-tert-butoxycarbonyl-2,2-dimethyl-4-phenyloxazolidine-5-carboxylate can be prepared in the following way:

0.96 g of (4S,5R)-3-tert-butoxycarbonyl-2,2-dimethyl-4-phenyloxazolidine-5-carboxylic acid, 0.66 g of N,N'-dicyclohexylcarbodiimide and 0.12 g of 4-dimethylaminopyridine are added to a solution of 1.46 g of 4-acetoxy-2α-benzoyloxy-1,13α-dihydroxy- 5β,20-epoxy-10β-methoxyacetyloxy-9-oxo-7β-triethylsilyloxy-11-taxene in 15 cm³ of toluene. The reaction mixture is heated with stirring for 3 hours at a temperature in the region of 80° C., then cooled to a temperature of 20° C. and poured into a mixture of 50 cm³ of dichloromethane and 150 cm³ of a saturated aqueous sodium hydrogencarbonate solution. The organic phase is separated by settling, washed with 2 times 20 cm³ of distilled water, dried over magnesium sulphate, filtered and then concentrated to dryness under reduced pressure (2.7 kPa) at 40° C. There are obtained 2.5 g of a white foam which is purified by chromatography on 75 g of silica (0.063–0.2 mm) contained in a column with a diameter of 3 cm [eluent: dichloromethane/methanol (99/1 by volume)], 3 cm³ fractions being collected. Fractions 42 to 59 are combined and concentrated to dryness under reduced pressure (2.7 kPa, then 0.07 kPa) at 40° C. There are thus obtained 1.9 g of 4-acetoxy-1-hydroxy- 2α-benzoyloxy-5β, 20-epoxy-10β-methoxyacetyloxy-9-oxo- 7β-triethylsilyloxy-11-taxen-13α-yl (4S,5R)-3-tert-butoxycarbonyl-2,2-dimethyl-4-phenyloxazolidine-5-carboxylate.

(4S,5R)-3-tert-Butoxycarbonyl-2,2-dimethyl-4-phenyloxazolidine-5-carboxylic acid can be prepared according to the method described in Application PCT WO 9209589.

4-Acetoxy-2α-benzoyloxy-1,13α-dihydroxy- 5β,20-epoxy-10β-methoxyacetyloxy-9-oxo-7β-triethylsilyloxy-11-taxene can be prepared in the following way:

2.71 g of methoxyacetyl chloride are added dropwise over 5 minutes and at a temperature in the region of 5° C. to a solution of 3.29 g of 4-acetoxy-2α-benzoyloxy-1,10β,13α-trihydroxy- 5β,20-epoxy-9-oxo-7β-triethylsilyloxy-11-taxene in 125 cm³ of anhydrous pyridine, maintained under an argon atmosphere. On completion of the addition, the reaction mixture is stirred for 14 hours at a temperature in the region of 5° C., then for 24 hours at a temperature in the region of 20° C. and poured into a mixture of 250 cm³ of dichloromethane and 1000 cm³ of a saturated aqueous sodium hydrogencarbonate solution. The organic phase is separated by settling, washed with 2 times 100 cm³ of distilled water, dried over magnesium sulphate, filtered and then concentrated to dryness under reduced pressure (2.7 kPa) at 40° C. There are obtained 4.1 g of a beige foam which is purified by chromatography on 80 g of silica (0.063–0.2 mm) contained in a column with a diameter of 3 cm [eluent: dichloromethane/methanol (99/1 by volume)]. The fractions which contain only the desired product are combined and concentrated to dryness under reduced pressure (2.7 kPa) at 40° C. There are thus obtained 2.9 g of 4-acetoxy-2α-benzoyloxy-1,13α-dihydroxy-5β,20-epoxy-10β-methoxyacetyloxy- 9-oxo-7β-triethylsilyloxy-11-taxene in the form of a white foam.

4-Acetoxy-2α-benzoyloxy-1,10β,13α-trihydroxy- 5β,20-epoxy-9-oxo-7β-triethylsilyloxy-11-taxene can be prepared according to the method described by J-N. Denis et al., J. Am. Chem. Soc., 110, 5917 (1988).

EXAMPLE 3

The electrolytic reduction of 4-acetoxy-2α-benzoyloxy-5β,20-epoxy- 1,7β,10β-trihydroxy-9-oxo-11-taxen-13α-yl (2R,3S)-3-tert-butoxycarbonylamino-3-phenyl-2-hydroxypropionate (or docetaxel) is carried out in an electrolysis cell having the following characteristics:

the cell is a 50 cm³ glass tank divided into 2 compartments by a cation-exchange membrane,
the cathode is a mercury sheet whose working surface area is approximately 4 cm²,
the anode is a platinum grid,
the reference electrode is a saturated calomel electrode.

| | |
|---|---|
| 4-acetoxy-2α-benzoyloxy-5β,20-epoxy-1,7β,10β-trihydroxy-9-oxo-11-taxen-13α-yl (2R,3S)-3-tert-butoxycarbonylamino-3-phenyl-2-hydroxypropionate (assaying at 73%, i.e. 293 mg of pure docetaxel) | 402 mg |
| methanol | 40 cm³ |
| tetraethylammonium tetrafluoroborate | 0.87 g |
| tetraethylammonium acetate | 2.61 g |
| acetic acid | 0.4 cm³ | are introduced into the cathode compartment.

Approximately 10 cm³ of a 1% by volume aqueous sulphuric acid solution are introduced into the anode compartment.

After deaerating the solution for 10 minutes by sparging with a stream of argon, the potential of the cathode is fixed at −1.85 volts at the beginning of the electrolysis. It is progressively reduced to −2.02 volts at the end of the electrolysis.

After passing 480 coulombs, electrolysis is halted. The solvent is evaporated under reduced pressure at a temperature below 35° C. The residue is taken up in 20 cm³ of water and extracted with 3 times 20 cm³ of dichloromethane. The organic phase is rinsed with 20 cm³ of saturated aqueous sodium chloride solution and then dried over magnesium sulphate. After filtration and evaporation of the solvent under reduced pressure at a temperature below 35° C., the crude product obtained is chromatographed on 50 g of silica (0.063–0.2 mm) contained in a column with a diameter of 24 mm. Elution is carried out with a dichloromethane/methanol mixture containing 1,2 and then 3% methanol by volume. The fractions containing the expected purified product are combined and concentrated to dryness under reduced pressure (0.27 kPa) at a temperature below 35° C. There are thus obtained, with a yield of 53%, 136 mg of 4-acetoxy-5β,20-epoxy- 1,2α,7β,10β-tetrahydroxy-9-oxo-11-taxen-13α-yl (2R,3S)-3-tert-butoxycarbonylamino-3-phenyl-2-hydroxypropionate in the form of a white foam.

The product thus obtained can be acylated in the 2-position after protection of the hydroxyl functional groups in the 7β- and 10β-positions and in the 2-position of the side chain.

EXAMPLE 4

The electrolytic reduction of 4-acetoxy-2α-benzoyloxy-5β,20-epoxy- 1,10β-dihydroxy-7α-triethylsilyloxy-9-oxo-11-taxen-13α-yl (2R,3S)-3-tert-butoxycarbonylamino-3-phenyl-2-(triethylsilyloxy)-propionate is carried out in an electrolysis cell having the following characteristics:

the cell is a 50 cm³ glass tank divided into 2 compartments by a cation-exchange membrane,
the cathode is a mercury sheet whose working surface area is approximately 12 cm²,
the anode is a platinum grid,
the reference electrode is a saturated calomel electrode.

| | |
|---|---|
| 4-acetoxy-2α-benzoyloxy-5β,20-epoxy-1,10β-dihydroxy-7α-triethylsilyloxy-9-oxo-11-taxen-13α-yl (2R,3S)-3-tert-butoxycarbonylamino-3-phenyl-2-(triethylsilyloxy)propionate | 500 mg |
| methanol | 25 cm³ |

-continued

| | |
|---|---|
| tetraethylammonium acetate | q.s. for 0.1 M |
| acetic acid | 0.05 cm³ | are introduced into the cathode compartment.

Approximately 25 cm³ of an identical solution which does not contain the substrate are introduced into the anode compartment.

The cell is immersed in a refrigerating bath containing melting ice. The temperature of the reaction mixture is in the region of 4° C. After deaerating the solution for 10 minutes by sparging with a stream of argon, the potential of the cathode is fixed at −1.95 volts at the beginning of electrolysis.

After passing 340 coulombs, electrolysis is halted. 6 volumes of a saturated aqueous sodium hydrogencarbonate solution, diluted to 50%, are added to the solution obtained. Extraction is carried out with 3 times 25 cm³ of ethyl acetate. The organic phase is rinsed with a saturated aqueous sodium chloride solution and then dried over magnesium sulphate. After filtration and evaporation of the solvent under reduced pressure at a temperature below 35° C., the crude product obtained is chromatographed on 50 g of silica contained in a column with a diameter of 20 mm. Elution is carried out with a dichloromethane/methanol mixture under a pressure of 4 bars. Fractions 12 to 59, which contain the expected purified product, are combined and concentrated to dryness under reduced pressure (0.27 kPa) at a temperature below 35° C. There are thus obtained, with a yield of 55%, 248 mg of 4-acetoxy- 5β,20-epoxy-1,2α,10β-trihydroxy-7α-triethylsilyloxy-9-oxo-11-taxen-13α-yl (2R,3S)-3-tert-butoxycarbonylamino-3-phenyl-2-(triethylsilyloxy)propionate in the form of a white foam.

The product thus obtained can be acylated in the 2-position after protection of the hydroxyl functional group in the 10β-position.

EXAMPLE 5

The electrolytic reduction of 10-deacetylbaccatin III is carried out in an electrolysis cell which has the following characteristics:

the cell is a 100 cm³ glass tank divided into two compartments by a cation-exchange membrane,
the cathode is a mercury sheet whose working surface area is approximately 12 cm²,
the anode is a platinum grid,
the reference electrode is a saturated calomel electrode.

50 cm³ of a solution containing:

| | |
|---|---|
| 10-deacetylbaccatin III | 500 mg |
| tetramethylammonium acetate | 0.1 M |
| acetic acid | 0.1 M |
| methanol | 50 cm³ | are introduced into the cathode compartment.

10 cm³ of a 0.15M aqueous sulphuric acid solution are introduced into the anode compartment.

After deaerating the solution for 10 minutes by sparging with a stream of argon, which is maintained throughout the duration of the electrolysis, the potential of the cathode is fixed at −1.9 volts with respect to the reference electrode.

The solution is electrolyzed for 160 minutes, that is to say for the time required for passing 700 coulombs (i.e. 7.6 faradays per mole). After having removed the solvent under reduced pressure at 35° C., the residue is taken up in 20 cm³ of ethyl acetate and 20 cm³ of water saturated with sodium chloride and buffered to pH=7 with a 0.2M aqueous sodium phosphate solution. After separating by settling, the aqueous phase is extracted with ethyl acetate (10 cm³ each time) until exhausted. After drying the organic phase over sodium sulphate, filtration and concentration to dryness under reduced pressure at a temperature in the region of 35° C., there are obtained 370 mg of a crude product which is purified by chromatography on a silica column (Kieselgel 60 F 254, Merck) with a diameter of 2 cm and with a height of 3 cm. Elution is carried out successively with 500 cm³ in total of a methanol/methylene chloride/ethyl acetate (5/47.5/47.5 by volume) mixture, 250 cm³ in total of a methanol/methylene chloride/ethyl acetate (10/45/45 by volume) mixture and 250 cm³ in total of a methanol/ethyl acetate (10/90 by volume) mixture. After evaporation of the fractions eluted between the 50th cm³ of the first eluent, all the second eluent and the first 90 cm³ of the last eluent, and drying the product obtained under reduced pressure (0.27 kPa), there are obtained 337.4 mg of 4,10β-diacetoxy-1,2α,7β,13α-tetrahydroxy- 5β,20-epoxy-9-oxo-11-taxene with a yield of 83%.

EXAMPLE 6

2.30 cm³ of a 1.4M solution of n-butyllithium in hexane and 510 mg of 4-methoxybenzoyl chloride are successively added, at a temperature in the region of −78° C., to a solution of 1.5 g of 4α-acetoxy-1β,2α-dihydroxy- 5β,20-epoxy-10β-methoxyacetoxy-9-oxo-7β-triethylsilyloxy-11-taxen-13α-yl (2R,4S,5R)-3-tert-butoxycarbonyl-2-(4-methoxyphenyl)-4-phenyl- 1,3-oxazolidine-5-carboxylate-in 20 cm³ of tetrahydrofuran kept stirring and under an argon atmosphere. The solution is thus kept stirred for 30 minutes and then 3 cm³ of a saturated aqueous ammonium chloride solution are added. The reaction mixture is brought to a temperature in the region of 20° C. over 1 hour. The solution obtained is poured into a mixture of 100 cm³ of ethyl acetate and 100 cm³ of a saturated aqueous ammonium chloride solution. The aqueous phase is. separated by settling and then extracted with 2 times 50 cm³ of ethyl acetate. The organic phases are combined, washed with 50 cm³ of distilled water, then dried over magnesium sulphate, filtered and concentrated to dryness under reduced pressure (2.7 kPa) at 40° C. There are obtained 2.15 g of a white foam which is purified by chromatography on 1500 g of silica (0.063–0.2 mm) contained in a column with a diameter of 4 cm [eluent: ethyl acetate/cyclohexane (30/70 by volume)], 10 cm³ fractions being collected. The fractions which contain only the desired product are combined and concentrated to dryness under reduced pressure (2.7 kPa) at 40° C. There is obtained 0.760 g of 4α-acetoxy-5β,20-epoxy-1β-hydroxy-10β-methoxyacetoxy-2α-( 4-methoxybenzoyloxy)-9-oxo-7β-triethylsilyloxy-11-taxen-13α-yl (2R, 4S, 5R)-3-tert-butoxycarbonyl-2-(4-methoxyphenyl)-4-phenyl-1,3-oxazolidine-5-carboxylate in the form of a white foam, the characteristics of which are the following:

N.M.R. spectrum: (400 MHz, CDCl₃, δ in ppm): 0.59 (q, J=7.5 Hz, 6H, —C$\underline{H}$2— ethyl, 0.93 (t, J=7.5 Hz, 9H, —C$\underline{H}_3$ ethyl), 1.10 (s, 9H, —C(C$\underline{H}_3$)₃), 1.19 (s, 3H, —C$\underline{H}_3$ 16 or 17), 1.20 (s, 3H, —C$\underline{H}_3$ 16 or 17), 1.67 (2, 3H, —C$\underline{H}_3$ 19), 1.70 (s, 3H, —C$\underline{H}_3$ 18), 1.73 (s, 1H, —O$\underline{H}$ at 1), 1.86 (mt, 1H, >(CH)—$\underline{H}$ 6), 1.87 (s, 3H, —COC$\underline{H}_3$), 2.12 and 2.20 (2 dd, J=16 and 9 Hz, each 1H, —C$\underline{H}_2$— 14), 2.49 (mt, 1H, >(CH)—$\underline{H}$ 6), 3.52 (s, 3H, —OC$\underline{H}_3$), 3.71 (d, J=7 Hz, 1H, —$\underline{H}$ 3), 3.83 (s, 3H, Ar—OC$\underline{H}_3$ at 5'), 3.89 (s, 3H, Ar—OC$\underline{H}_3$ at 2), 4.10 (d, J=8 Hz, 1H, >(CH)—H]20), 4.18 (limit AB, J=16 Hz, 2H, —OCOCH₂O—), 4.24 (d, J=8 Hz, 1H, >(CH)—H 20), 4.43 (dd, J=11 and 7 Hz, 1H, —H 7), 4.58 (d, J=5.5 Hz, 1H, —H 2'), 4.86 (broad d, J=10 Hz, 1H, —H 5), 5.43 (d, J=5.5 Hz, 1H, —H 3'), 5.62 (d, J=7 Hz, 1H, —H 2) 6.07 (t, J=9 Hz, 1H, —H 13), 6.39 (broad s, 1H, —H 5'), 6.44 (s, 1H, —H 10), 6.93 (d, J=7.5 Hz, 2H, —C₆H₅ at 5' (—H 3 and —H 5)); 6.98 (d, J=8.5 Hz, 2H, aromatic —H ortho to —OCH₃), from 7.30 to 7.45 (mt, 7H, —C₆H₅ at 3' and C₆H₅ at 5' (—H 2 and —H 6)), 7.99 (d, J=8.5 Hz, 2H, aromatic —H meta to —OCH₃).

A solution of 0.750 g of 4α-acetoxy-5β,20-epoxy -1β-hydroxy-10β-methoxyacetoxy-2α -(4methoxybenzoyloxy) -9-oxo-7β-triethylsilyloxy-11-taxen-13α-yl (2R,4S,5R)-3-tert-butoxycarbonyl-2-(4-methoxyphenyl)- 4-phenyl-1,3 -oxazolidine-5-carboxylate in 13 cm³ of a 0.1N ethanolic hydrochloric acid solution is kept stirring at a temperature in the region of 20° C. for 16 hours. The reaction mixture is concentrated to dryness under reduced pressure (2.7 kPa) at 40° C. The crude reaction product is dissolved in 100 cm³ of dichloromethane and 100 cm³ of a saturated aqueous sodium bicarbonate solution. The organic phase is separated by settling and then extracted with 2 times 50 cm³ of dichloromethane. The organic phases are combined, washed with 50 cm³ of distilled water, then dried over magnesium sulphate, filtered and concentrated to dryness under reduced pressure (2.7 kPa) at 40° C. There is obtained 1.0 g of a white foam which is purified by chromatography on 1000 g of silica (0.063–0.2 mm) contained in a column with a diameter of 4 cm [eluent: ethyl acetate/cyclohexane (30/70 by volume)], 10 cm³ fractions being collected. The fractions which only contain the desired product are combined and concentrated to dryness under reduced pressure (2.7 kPa) at 40° C. There is obtained 0.250 g of 4α-acetoxy-1β,7β-dihydroxy-5β,20-epoxy-10β-methoxyacetoxy-2α-(4-methoxybenzoyloxy)- 9 -oxo-11-taxen-13α-yl (2R, 3S)-3-tert-butoxycarbonylamino-2-hydroxy-3-phenylpropionate in the form of a white foam, the characteristics of which are the following:

N.M.R. spectrum: (400 MHz, CDCl₃, δ in ppm): 1.15 (s, 3H, —CH₃ 16 or 17), 1.27 (s, 3H, —CH₃ 16 or 17), 1.36 (s, 9H, —(CH₃)₃), 1.69 (s, 3H, —CH₃ 19), from 1.80 to 1.95 (mt, 1H, >(CH) —H 6), 1.87 (s, 3H, —CH₃ 18), 2.30 (mt, 2H, —CH₂— 14), 2.40 (s, 3H, —COCH₃), 2.55 (mt, 1H, >(CH) —H 6), 3.49 (s, 3H, —OCH₃), 3.78 (d, J=7 Hz, 1H, —H 3), 3.89 (s, 3H, Ar—OCH₃), 4.17 (d, J=8 Hz, 1H, >(CH)—H 20), 4.24 (limit AB, J=16 Hz, 2H, —OCOCH₂O—), 4.31 (d, J=8 Hz, 1H, >(CH) —H 20), 4.43 (dd, J=11 and 7 Hz, 1H, —H 7), 4.64 (broad s, 1H, —H 2'), 4.95 (broad d, J=10 Hz, 1H, —H 5), 5.25 (broad d, J=10 Hz, 1H, —H 3'), 5.52 (d, J=10 Hz, 1H, —CONH—), 5.64 (d, J=7 Hz, 1H, —H 2), 6.22 (t, J=9 Hz, 1H, —H 13), 6.40 (s, 1H, —H 10), 6.98 (d, J=8.5 Hz, 2H, aromatic —H ortho to —OCH₃), from 7.25 to 7.45 (mt, 5H, —C₆H₅ at 3'), 8.05 (d, J=8.5 Hz, 2H, aromatic —H meta to —OCH₃).

EXAMPLE 7

0.700 g of zinc iodide are successively added to a solution of 0.200 g of 4α-acetoxy-1β,7β-dihydroxy- 5β,20-epoxy-10β-methoxyacetoxy-2α-(4-methoxybenzoyloxy)-9-oxo-11-taxen-13α-yl (2R,3S)-3-tert-butoxycarbonylamino-2-hydroxy-3-phenylpropionate in 15 cm³ of methanol kept stirring at a temperature in the region of 25° C. The solution is thus kept stirred for 5 hours and then 10 cm³ of distilled water are added. The reaction mixture is filtered and the precipitate is rinsed with 5 cm³ of ethyl acetate and 5 cm³ of distilled water. The organic phase is separated by settling. The aqueous phase is concentrated under reduced pressure (2.7 kPa) and taken up in 20 cm³ of ethyl acetate and 20 cm³ of distilled water. The organic phases are combined and washed with 20 cm³ of a saturated sodium thiosulphate solution and 20 cm³ of distilled water. The organic phase is dried over magnesium sulphate, filtered and concentrated to dryness under reduced pressure (2.7 kPa). There is obtained 0.100 g of a yellow oil which is purified by preparative chromatography on a silica plate with a thickness of 2 mm [eluent: dichloromethane/methanol (95/5 by volume)]. There is thus obtained 0.048 mg of 4α-acetoxy-5β,20-epoxy-2α-(4-methoxybenzoyloxy)-9-oxo- 1β,7β,10β-trihydroxy-11-taxen-13α-yl (2R, 3S)-3-tert-butoxycarbonylamino-2-hydroxy-3-phenylpropionate in the form of a white foam, the characteristics of which are the following:

N.M.R. spectrum: (400 MHz, CDCl₃, δ in ppm): 1.14 (s, 3H, —CH₃ 16 or 17), 1.24 (s, 3H, —CH₃ 16 or 17), 1.37 (s, 9H, —(CH₃)₃), 1.72 (s, 1H, —OH at 1), 1.78 (s, 3H, —CH₃ 19), from 1.75 to 1.90 (mt, 1H, >(CH) —H6), 1.87 (s, 3H, —CH₃ 18), 2.28 (d, J=9 Hz, 2H, —CH₂— 14), 2.40 (s, 3H, —COCH₃), 2.61 (mt, 1H, >(CH) —H6), 3.32 (d, J=4.5 Hz, 1H, —OH at 2'), 3.89 (s, 3H, —OCH₃), 3.92 (d, J=7 Hz, 1H, —H 3), 4.20 (d, J=8 Hz, 1H, >(CH) —H 20), 4.21 (broad s, 1H, —OH at 10), 4.23 (mt, 1H, —H 7), 4.33 (d, J=8 Hz, 1H, >(CH) —H 20), 4.63 (mt, 1H, H 2'), 4.95 (broad d, J=10 Hz, 1H, —H 5), 5.21 (broad s, 1H, —H 10), 5.27 (broad d, J=10 Hz, 1H, —H 3'), 5.43 (d, J=10 Hz, 1H, —CONH—), 5.67 (d, J=7 Hz, 1H, —H 2), 6.23 (t, J=9 Hz, 1H, —H 13), 6.98 (d, J=8.5 Hz, 2H, aromatic —H ortho to —OCH₃) , from 7.25 to 7.45 (mt, 5H, —C₆H₅ at 3'), 8.08 (d, J=8.5 Hz, 2H, aromatic —H meta to —OCH₃).

EXAMPLE 8

4α-Acetoxy-5β,20-epoxy-2α-(4-fluorobenzoyloxy)-1β-hydroxy-10β-methoxyacetoxy- 9-oxo-7β-triethylsilyloxy-11-taxen-13α-yl (2R, 4S, 5R) -3 -tert-butoxycarbonyl- 2-(4-methoxyphenyl)-4-phenyl-1,3-oxazolidine-5-carboxylate is obtained by carrying out the reaction as in Example 6 from appropriate starting materials and has the following characteristics:

N.M.R. spectrum: (400 MHz, CDCl₃, δ in ppm): 0.60 (q, J=7.5 Hz, 6H, —CH₂— ethyl, 0.94 (t, J=7.5 Hz, 9H, —CH₃ ethyl), 1.08 (s, 9H, —C(CH₃)₃), 1.18 (s, 3H, —CH₃ 16 or 17), 1.19 (s, 3H, —CH₃ 16 or 17), 1.65 (s, 3H, —CH₃ 19), 1.68 (s, 3H, —CH 18), 1.71 (s, 1H, —OH at 1), 1.86 (mt, 1H, >(CH) —H 6) , 1.87 (s, 3H, —COCH₃), 2.09 and 2.18 (2 dd, J=16 and 9 Hz, each 1H, —CH₂— 14), 2.48 (mt, 1H, >(CH) —H 6), 3.52 (s, 3H, —OCH₃), 3.72 (d, J=7 Hz, 1H, —H 3), 3.81 (s, 3H, Ar—OCH₃), 4.09 (d, J=8 Hz, 1H, >(CH) —H 20), 4.16 (limit AB, J=16 Hz, 2H, —OCOCH₂O—), 4.19 (d, J=8 Hz, 1H, >(CH) —H 20), 4.43 (dd, J=11 and 7 Hz, 1H, —H 7), 4.57 (d, J=5.5 Hz, 1H, —H 2'), 4.85 (broad d, J=10 Hz, 1H, —H 5), 5.43 (d, J=5.5 Hz, 1H, —H 3'), 5.60 (d, J=7 Hz, 1H, —H 2), 6.06 (t, J=9 Hz, 1H, —H 13), 6.39 (broad s, 1H, —H 5'), 6.43 (s, 1H, —H 10), 6.92 (d, J=7.5 Hz, 2H, —C₆H₅ at 5' (—H 3 and —H 5)), 7.13 (t, J=8.5 Hz, 2H, aromatic —H ortho to —F), from 7.30 to 7.45 (mt, 7H, —C₆H₅ at 3' and C₆H₅ at 5' (—H 2 and —H 6)), 8.03 (d, J=8.5 Hz, 2H, aromatic —H meta to —F).

4α-Acetoxy-1β,7β-dihydroxy-5 β,20-epoxy-2α-(4-fluorobenzoyloxy)-10β-methoxyacetoxy-9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl₃, δ in ppm): 1.15 (s, 3H, —CH₃ 16 or 17), 1.27 (s, 3H, —CH₃ 16 or 17), 1.35 (s, 9H, —C(CH₃)₃), 1.70 (s, 3H, —CH₃ 19), 1.87 (s, 3H, —CH₃ 18), 1.89 (mt, 1H, >(CH) —H 6), 2.27 and 2.33 (2 dd, J=17 and 9 Hz, each 1H, —CH₂— 14), 2.40 (s, 3H, —COCH₃), 2.58 (mt, 1H, >(CH) —H 6), 3.33 (broad unresolved peak, 1H, —OH at 2'), 3.53 (s, 3H, —OCH₃), 3.81 (d, J=7 Hz, 1H, —H 3), 4.17 (d, J=8 Hz, 1H, >(CH) —H 20), 4.26 (limit AB, J=16 Hz, 2H, —OCOCH₂O—), 4.29 (d, J=8 Hz, 1H, >(CH) —H 20), 4.42 (dd, J=11 and 7 Hz, 1H, —H 7), 4.66 (broad s, 1H, —H 2'), 4.96 (dd, J=10 and 1.5 Hz, 1H, —H 5), 5.27 (broad d, J=10 Hz, 1H, —H 3'), 5.37 (d, J=10 Hz, 1H, —CONH—), 5.66 (d, J=7 Hz, 1H, —H 2), 6.25 (broad t, J=9 Hz, 1H, —H 13), 6.39 (s, 1H, —H 10), 7.19 (t, J=8.5 Hz, 2H, aromatic —H ortho to –F) , from 7.30 to 7.45 (mt, 5H, —C₆H₅ at 3'), 8.13 (dd, J=8.5 and 6 Hz, 2H, aromatic —H meta to —F).

EXAMPLE 9

4α-Acetoxy-5β,20-epoxy-2α-(4-fluorobenzoyloxy)-9-oxo-1β,7β,10β-trihydroxy-11-taxen-13α-yl (2R,3S)-3-tert-butoxycarbonylamino-2-hydroxy-3-phenylpropionate is obtained by carrying out the reaction as in Example 7 and has the following characteristics:

N.M.R. spectrum: (400 MHz, CDCl₃, δ in ppm): 1.14 (s, 3H, —CH₃ 16 or 17), 1.26 (s, 3H, —CH₃ 16 or 17), 1.37 (s, 9H, —(CH₃)₃), 1.63 (s, 1H, —OH at 1), 1.77 (s, 3H, —CH₃ 19), 1.86 (mt, 1H, >(CH) —H 6), 1.87 (s, 3H, —CH₃ 18), 2.28 (d, J=9 Hz, 2H, —CH₂— 14), 2.39 (s, 3H, —COCH₃), 2.60 (mt, 1H, >(CH) —H 6), 3.33 (unresolved peak, 1H, —OH at 2'), 3.92 (d, J=7 Hz, 1H, —H 3), 4.19 (d, J=8 Hz, 1H, >(CH) —H 20), 4.21 (broad s, 1H, —OH at 10), 4.24 (mt, 1H, —H 7), 4.31 (d, J=8 Hz, 1H, > (CH) —H 20), 4.64 (broad s, 1H, —H 2'), 4.96 (dd, J=10 and 1.5 Hz, 1H, —H 5), 5.21 (s, 1H, —H 10), 5.27 (broad d, J=10 Hz, 1H, —H 3'), 5.43 (d, J=10 Hz, 1H, —CONH—), 5.67 (d, J=7 Hz, 1H, —H 2), 6.24 (t, J=9 Hz, 1H, —H 13), 7.19 (t, J=8.5 Hz, 2H, aromatic —H ortho to —F) , from 7.25 to 7.45 (mt, 5H, —C₆H₅ at 3'), 8.12 (dd, J=8.5 and 6 Hz, 2H, aromatic —H meta to —F).

EXAMPLE 10

4α-Acetoxy-5β,20-epoxy-2α-[4-(trifluoromethyl)benzoyloxy]-1β-hydroxy- 10β-methoxyacetoxy-9-oxo-7β-triethylsilyloxy-11-taxen-13α-yl (2R, 4S, 5R)-3-tert-butoxycarbonyl-2-(4methoxyphenyl)- 4-phenyl-1,3-oxazolidine-5-carboxylate is obtained by carrying out the reaction as in Example 6 from appropriate starting materials and has the following characteristics:

N.M.R. spectrum: (400 MHz, CDCl₃, δ in ppm): 0.60 (q, J=7.5 Hz, 6H, —CH₂— ethyl, 0.96 (t, J=7.5 Hz, 9H, —CH₃ ethyl), 1.09 (s, 9H, —C(CH₃)₃), 1.18 (s, 3H, —CH₃ 16 or 17), 1.20 (s, 3H, —CH₃ 16 or 17), 1.64 (s, 1H, —OH at 1) 1.66 (s, 3H, —CH₃ 19), 1.68 (s, 3H, —CH₃ 18), 1.86 (mt, 1H, >(CH) —H 6), 1.90 (s, 3H, —COCH₃), 2.11 and 2.19 (2 dd, J=15 and 9 Hz, each 1H, —CH₂— 14), 2.50 (mt, 1H, >(CH) —H 6), 3.52 (s, 3H, —OCH₃), 3.73 (d, J=7 Hz, 1H, —H 3), 3.82 (s, 3H, Ar—OCH₃), 4.10 (d, J=8 Hz, 1H, >(CH) —H 20), 4.17 (limit AB, J=16 Hz, 2H, —OCOCH₂O—), 4.20 (d, J=8 Hz, 1H, >(CH) —H 20), 4.43 (dd, J=11 and 7 Hz, 1H, —H 7), 4.58 (d, J=5 Hz, 1H, —H 2'), 4.86 (broad d, J=10 Hz, 1H, —H 5), 5.45 (d, J=5 Hz, 1H, —H 3'), 5.63 (d, J=7 Hz, 1H, —H 2), 6.05 (t, J=9 Hz, 1H, —H 13), 6.40 (broad s, 1H, —H 5'), 6.45 (s, 1H, —H 10), 6.92 (d, J=7.5 Hz, 2H, —C₆H₅ at 5' (—H 3 and —H 5)), from 7.35 to 7.45 (mt, 7H, —C₆H₅ at 3' and —C₆H₅ at 5' (—H 2 and —H 6)); 7.76 (d, J=8.5 Hz, 2H, aromatic —H ortho to —CF₃), 8.14 (d, J=8.5 Hz, 2H, aromatic —H meta to —CF₃).

4α-Acetoxy-1β,7β-dihydroxy-5β,20-epoxy-2α-[4-(trifluoromethyl)benzoyloxy]- 10β-methoxyacetoxy-9-oxo-11-taxen-13α-yl (2R, 3S) -3-tert-butoxycarbonylamino-2-hydroxy-3-phenylpropionate is obtained by carrying out the reaction as in Example 6 and has the following characteristics:

N.M.R. spectrum: (400 MHz, CDCl₃, δ in ppm): 1.16 (s, 3H, —CH₃ 16 or 17), 1.28 (s, 3H, —CH₃ 16 or 17), 1.32 (s, 9H, —(CH₃)₃), 1.70 (s, 3H, —CH₃ 19), from 1.85 to 1.95 (mt, 1H, >(CH) —H 6), 1.90 (s, 3H, —(CH₃) 18), 2.31 (split limit AB, J=18 and 9 Hz, 2H, —CH₂— 14), 2.42 (s, 3H, —COCH₃), 2.58 (mt, 1H, >(CH) — H 6), from 3.20 to 3.60 (broad unresolved peak, 1H, —OH at 2'), 3.52 (s, 3H, —OCH₃), 3.84 (d, J=7 Hz, 1H, —H 3), 4.18 (d, J=8 Hz, 1H, >(CH) —H 20), 4.26 (limit AB, J=16 Hz, 2H, —OCOCH₂O—), 4.28 (d, J=8 Hz, 1H, >(CH) —H 20), 4.43 (dd, J=11 and 7 Hz, 1H, H 7), 4.68 (broad s, 1H, —H 2'), 4.96 (broad d, J=10 Hz, 1H, —H 5), 5.30 (broad d, J=10 Hz, 1H, —H 3'), 5.42 (d, J =10 Hz, 1H, —CONH—), 5.67 (d, J=7 Hz, 1H, —H 2), 6.28 (t, J=9 Hz, 1H, —H 13), 6.40 (s, 1H, —H 10), from 7.30 to 7.45 (mt, 5H, —C₆H₅ at 3'), 7.79 (d, J=8.5 Hz, 2H, aromatic —H ortho to —CF₃), 8.24 (d, J=8.5 Hz, 2H, aromatic —H meta to —CF₃).

EXAMPLE 11

4α-Acetoxy-5β,20-epoxy-2α-[4-(trifluoromethyl)benzoyloxy]-9-oxo- 1β,7β,10β-trihydroxy-11-taxen-13α-yl (2R,3S)-3-tert-butoxycarbonylamino-2-hydroxy-3-phenylpropionate is obtained by carrying out the reaction as in Example 7 and has the following characteristics:

N.M.R. spectrum: (400 MHz, CDCl₃, δ in ppm): 1.14 (s, 3H, —CH₃ 16 or 17), 1.26 (s, 3H, —CH₃ 16 or 17), 1.34 (s, 9H, —(CH₃)₃) , 1.79 (s, 3H, —CH₃ 19) , from 1.80 to 1.95 (mt, 1H, >(CH) —H 6), 1.89 (s, 3H, —CH₃ 18), 2.28 (mt, 2H, —CH₂— 14), 2.42 (s, 3H, —COCH₃), 2.61 (mt, 1H, >(CH) —H 6), 3.32 (unresolved peak, 1H, —OH at 2'), 3.95 (d, J=7 Hz, 1H, —H 3), from 4.10 to 4.35 (broad unresolved peak, 1H, —OH at 10), 4.19 (d, J=8 Hz, 1H, >(CH) —H 20), 4.25 (mt, 1H, —H 7), 4.29 (d, J=8 Hz, 1H, >(CH) —H 20), 4.66 (broad s, 1H, H 2', 4.96 (broad d, J=10 Hz, 1H, —H 5), 5.21 (s, 1H, —H 10), 5.30 (broad d, J=10 Hz, 1H, —H 3'), 5.41 (d, J=10 Hz, 1H, —CONH—), 5.68 (d, J=7 Hz, 1H, —H 2), 6.27 (mt, 1H, —H 13), from 7.30 to 7.45 (mt, 5H, —C₆H₅ at 3'), 7.80 (d, J=8.5 Hz, 2H, aromatic —H ortho to —CF₃), 8.20 (d, J=8.5 Hz, 2H, aromatic —H meta to —CF₃).

EXAMPLE 12

4α-Acetoxy-5β,20-epoxy-2α-(2-fluorobenzoyloxy)-1β-hydroxy- 10β-methoxyacetoxy-9-oxo-7β-triethylsilyloxy-11-taxen-13α-yl (2R, 4S, 5R)-3-tertbutoxycarbonyl-2-(4-methoxyphenyl)- 4-phenyl-1,3-oxazolidine-5-carboxylate is obtained by carrying out the reaction as in Example 6 from appropriate starting materials and has the following characteristics:

N.M.R. spectrum: (400 MHz, CDCl₃, δ in ppm): 0.60 (q, J=7.5 Hz, 6H, —CH₂— ethyl, 0.94 (t, J=7.5 Hz, 9H, —CH₃ ethyl), 1.10 (s, 9H, —C(CH₃)₃), 1.19 (s, 3H, —CH₃ 16 and, —CH₃17), 1.68 (s, 3H, —CH₃ 19), 1.69 (s, 3H, —CH₃ 18), 1.74 (s, 1H, —OH at 1), 1.81 (s, 3H, —COCH₃), 1.86 (mt, 1H, >(CH) —H 6), 2.17 and 2.22 (2 dd, J=15 and 9 Hz, each 1H, —CH₂— 14), 2.48 (mt, 1H, >(CH)—H 6), 3.52 (s, 3H, —OCH$_3$, 3.71 (d, J=7 Hz, 1H, —H 3), 3.82 (s, 3H, Ar—OCH$_3$), from 4.10 to 4.25 (mt, 4H, —OCOCH$_2$O— and —CH$_2$— 20), 4.42 (dd, J=11 and 7 Hz, 1H, —H 7), 4.58 (d,J=5 Hz, 1H, —H 2'), 4.86 (broad d, J=10 Hz, 1H, —H 5), 5.45 (very broad s, 1H, —H 3'), 5.67 (d, J=7 Hz, 1H, —H 2), 6.08 (t,J=9 Hz, 1H, —H 13), 6.40 (very broad s, 1H, —H5'), 6.45 (s, 1H, —H 10), 6.92 (d, J=7.5 Hz, 2H, —C$_6$H$_5$ at 5'(—H 3 and —H 5)), 7.16 (mt, 1H, —C$_6$H$_5$ at 2 (—H 3)), 7.28 (t, J=8.5 Hz, 1H, —C$_6$H$_5$ at 2 (—H5)), from 7.35 to 7.45 (mt, 7H, —C$_6$H$_5$ at 3' and —C$_6$H$_5$ at 5'(—H 2 and —H 6)), 7.58 (mt, 1H, —C$_6$H$_5$ at 2 (—H 4)), 7.96 (dd, J=8.5 and 8 Hz, 1H, —C$_6$H$_5$ at 2 (—H 6))

4α-Acetoxy-1β,7β-dihydroxy-5β,20-epoxy-2α-(2-fluorobenzoyloxy)-10β-methoxyacetoxy- 9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl$_3$, δ in ppm): 1.16 (s, 3H, —CH$_3$ 16 or 17), 1.26 (s, 3H, —CH$_3$ 16 or 17), 1.40 (s, 9H, —(CH$_3$)$_3$), 1.72 (s, 3H, —CH$_3$ 19), 1.88 (s, 3H, —CH$_3$ 18), 1.92 (mt, 1H, >(CH)— 6), 2.32 (s, 3H, —COCH$_3$), 2.33 (mt, 2H, —CH$_2$— 14), 2.56 (mt, 1H, >(CH)—H 6), 3.52 (s, 3H, —OCH$_3$), 3.79 (d, J=7 Hz, 1H, —H 3), 4.26 (limit AB, J=17 Hz, 2H, —OCOCH$_2$O—), 4.28 (limit AB, J=8 Hz, 2H, —CH$_2$— 20), 4.40 (dd, J=11 and 7 Hz, 1H, —H 7), 4.61 (broad s, 1H, —H 2'), 4.95 (broad d, J =10 Hz, 1H, —H 5), 5.24 (large d, J=10 Hz, 1H, —H 3'), 5.47 (d, J=10 Hz, 1H, —CONH—, 5.70 (d, J=7 Hz, 1H, —H 2), 6.19 (broad t, J=9 Hz, 1H, —H 13), 6.38 (s, 1H, —H 10), 7.20 (dd, J=10.5 and 8.5 Hz, 1H, —C$_6$H$_5$ at 2 (—H 3)), 7.28 (t, J=8.5 Hz, 1H, —C$_6$H$_5$ at 2 (—H 5)), from 7.30 to 7.45 (mt, 5H, —C$_6$H$_5$ at 3'), 7.60 (mt, 1H, —C$_6$H$_5$ at 2 (—H 4)), 8.03 (dd, J=8.5 and 8 Hz, 1H, —C$_6$H$_5$ at 2 (—H 6)).

EXAMPLE 13

4α-Acetoxy-5β,20-epoxy-2α-(2-fluorobenzoyloxy) -9-oxo-1β,7β,10β-trihydroxy-11-taxen-13α-yl (2R, 3S) -3-tert-butoxycarbonylamino-2-hydroxy-3-phenylpropionate is obtained by carrying out the reaction as in Example 7 and has the following characteristics:

N.M.R. spectrum: (400 MHz, CDCl$_3$, δ in ppm): 1.13 (s, 3H, —CH$_3$ 16 or 17), 1.24 (s, 3H, —CH$_3$ 16 or 17), 1.38 (s, 9H, —(CH$_3$)$_3$), 1.73 (s, 1H, —OH at 1), 1.78 (s, 3H, ——CH$_3$ 19), 1.84 (s, 3H, —CH$_3$ 18), 1.85 (mt, 1H, >(CH)—H 6), 2.30 (mt, 2H, —CH$_2$— 14), 2.30 (s, 3H, —COCH$_3$), 2.58 (mt, 1H, >(CH) —H 6), 3.43 (d, J=5.5 Hz, 1H, —OH at 2'), 3.90 (d, J=7 Hz, 1H, —H 3), 4.23 (broad s, 1H, —OH at 10), 4.23 (mt, 1H, —H 7), 4.28 (limit AB, J =9 Hz, 2H, —CH$_2$— 20), 4.60 (broad s, 1H, —H 2'), 4.94 (dd, J=10 and 1.5 Hz, 1H, —H 5), 5.21 (s, 1H, —H 10), 5.25 (broad d, J=10 Hz, 1H, —H 3'), 5.49 (d, J=10 Hz, 1H, —CONH—), 5.70 (d, J=7 Hz, 1H, —H 2), 6.19 (t, J=9 Hz, 1H, —H 13), 7.20 (dd, J=10.5 and 8.5 Hz, 1H, —C$_6$H$_5$ at 2 (—H 3)), 7.29 (t, J=8.5 Hz, 1H, —C$_6$H$_5$ at 2 (—H 5)), from 7.30 to 7.45 (mt, 5H, —C$_6$H$_5$ at 3'), 7.59 (mt, 1H, —C$_6$H$_5$ at 2 (—H 4)), 8.03 (dd, J=8.5 and 8 Hz, 1H, —C$_6$H$_5$ at 2 (—H 6)).

EXAMPLE 14

4α-Acetoxy-5β,20-epoxy-2α-(4-tert-butylbenzoyloxy)-1β-hydroxy-10β-methoxyacetoxy-9-oxo- 7β-triethylsilyloxy-11-taxen-13α-yl (2R, 4S, 5R)-3-tert-butoxycarbonyl 2-(4-methoxyphenyl)-4-phenyl-1,3-oxazolidine-5-carboxylate is obtained by carrying out the reaction as in Example 6 from appropriate starting materials and has the following characteristics:

N.M.R. spectrum: (400 MHz, CDCl$_3$, δ in ppm): 0.60 (q, J=7.5 Hz, 6H, —CH$_2$— ethyl, 0.93 (t,J=7.5 Hz, 9H, —CH$_3$ ethyl), 1.10 (s, 9H, —C(CH$_3$)$_3$), 1.18 (s, 3H, —CH$_3$ 16 or 17), 1.21 (s, 3H, —CH$_3$ 16 or 17), 1.38 (s, 9H, Ar-(CH$_3$)$_3$), 1.66 (s, 3H, —CH$_3$ 19), 1.68 (s, 1H, —OH at 1), 1.70 (s, 3H, —CH$_3$ 18), 1.87 (mt, 1H, >(CH) —H 6), 1.90 (s, 3H, —COCH$_3$), 2.13 and 2.20 (2 dd, J=16 and 9 Hz, each 1H, —CH$_2$— 14), 2.49 (mt, 1H, >(CH) —H 6), 3.52 (s, 3H, —OCH$_3$), 3.73 (d, J=7 Hz, 1H, —H 3), 3.82 (s, 3H, Ar—OCH$_3$), 4.12 (d, J=8.5 Hz, 1H, >(CH) —H 20), 4.15 (limit AB, J=16 Hz, 2H, —OCOCH$_2$O—), 4.27 (d, J=8.5 Hz, 1H, >(CH) —H 20), 4.44 (dd, J=11 and 6.5 Hz, 1H, —H 7), 4.58 (d, J=5 Hz, 1H, —H 2'), 4.87 (broad d, J=10 Hz, 1H, —H 5), 5.44 (d, J=5 Hz, 1H, —H 3'), 5.63 (d, J=7 Hz, 1H, —H 2), 6.06 (t,J=9 Hz, 1H, —H 13), 6.38 (s, 1H, —H 5'), 6.44 (s, 1H, —H 10), 6.92 (d, J=8.5 Hz, 2H, —C$_6$H$_5$ at 5' (—H 3 and H 5)), from 7.35 to 7.45 (mt, 7H, —C$_6$H$_5$ at 3' and —C$_6$H$_5$ at 5' (—H 2 and —H 6)), 7.49 (d, J=8.5 Hz, 2H, aromatic —H ortho to —C(CH$_3$)$_3$), 7.97 (d, J=8.5 Hz, 2H, aromatic —H meta to —C(CH$_3$)$_3$).

4α-Acetoxy-1β,7β- dihydroxy-5β,20-epoxy-2α-(4-tert-butylbenzoyloxy)-10β-methoxyacetoxy-9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl$_3$, δ in ppm): 1.15 (s, 3H, —CH$_3$ 16 or 17), 1.28 (s, 3H, —CH$_3$ 16 or 17), 1.35 (s, 18H, —(CH$_3$)$_3$), 1.70 (s, 3H, —CH$_3$ 19), 1.75 (s, 1H, —OH at 1), 1.88 (s, 3H, —CH$_3$ 18), 1.90 (mt, 1H, >(CH)-H 6), 2.28 and 2.37 (2 dd, J=16 and 9 Hz, each 1H, —CH$_2$—14), 2.36 (d, J=3.5 Hz, 1H, —OH at 7), 2.41 (s, 3H, —COCH$_3$), 2.58 (mt, 1H, >(CH) —H 6), 3.34 (d, J=Hz, 1H, —OH at 2'), 3.54 (s, 3H, OCH$_3$), 3.82 (d, J=7 Hz, 1H, —H 3), 4.19 (d, J=8.5 Hz, 1H, >(CH) —H 20), 4.28 (limit AB, J=16 Hz, 2H, —OCOCH$_2$O—), 4.36 (d, J=8.5 Hz, 1H, >(CH) —H 20), 4.43 (mt, 1H, —H 7), 4.63 (broad d, J=5 Hz, 1H, —H 2'), 4.97 (broad d, J=10 Hz, 1H, —H 5), 5.28 (broad d, J=10 Hz, 1H, —H 3'), 5.38 (d, J=10 Hz, 1H, —CONH—), 5.69 (d, J=7 Hz, 1H, —H 2), 6.25 (t, J=9 Hz, 1H, —H13), 6.40 (s, 1H, —H 10), from 7.30 to 7.45 (mt, 5H, —C$_6$H$_5$ at 3'), 7.52 (d, J=8.5 Hz, 2H, aromatic —H ortho to —C(CH$_3$)$_3$) , 8.05 (d, J=8.5 Hz, 2H, aromatic —H meta to —C(CH$_3$)$_3$).

EXAMPLE 15

4α -Acetoxy- 5β,20- epoxy-2α-(4-tert-butylbenzoyloxy)-9-oxo- 1β,7β,10β-trihydroxy-11-taxen-13α-yl (2R, 38)-3-tert-butoxycarbonylamino-2-hydroxy-3-phenylpropionate is obtained by carrying out the reaction as in Example 7 and has the following characteristics:

N.M.R. spectrum: (400 MHz, CDCl$_3$, δ in ppm): 1.14 (s, 3H, —CH$_3$ 16 or 17), 1.25 (s, 3H, —CH$_3$ 16 or 17), 1.37 (s, 18 H, —(CH$_3$)$_3$), 1.72 (s, 1H, —OH at 1), 1.77 (s, 3H, —CH$_3$ 19), 1.85 (mt, 1H, >(CH) —H 6), 1.86 (s, 3H, —CH$_3$ 18), 2.28 (limit AB, J=16 and 9 Hz, 2H, —CH$_2$—14), 2.42 (s, 3H, —COCH$_3$), 2.60 (mt, 1H, >(CH) —H 6], 3.38 (d, J=5.5 Hz, 1H, —OH at 2'), 3.92 (d, J=7 Hz, 1H, —H 3), 4.20 (d, J=8 Hz, 1H, >(CH) —H 20), 4.23 (broad s, 1H, —OH at 10), 4.25 (mt, 1H, —H 7), 4.36 (d, J=8 Hz, 1H, >(CH) —H 20), 4.64 (mt, 1H, —H 2'), 4.96 (broad d, J=10 Hz, 1H, —H 5), 5.22 (broad s, 1H, —H 10), 5.28 (broad d, J=10 Hz, 1H, —H 3'), 5.46 (d, J=10 Hz, 1H, —CONH—), 5.68 (d, J=7 Hz, 1H, —H 2), 6.23

(t, J=9 Hz, 1H, —H 13), from 7.30 to 7.45 (mt, 5H, —C₆H₅ at 3'), 7.52 (d, J=8 Hz, 2H, aromatic —H ortho to —C(CH₃)₃), 8.04 (d, J=8 Hz, 2H, aromatic —H meta to —C(CH₃)₃).

EXAMPLE 16

4α-Acetoxy-5β,20-epoxy-2α-(4-nitrobenzoyloxy)-1β-hydroxy- 10β-methoxyacetoxy-9-oxo-7β-triethylsilyloxy-11-taxen-13α-yl (2R, 4S, 5R)-3-tert-butoxycarbonyl-2-(4-methoxyphenyl)-4-phenyl-1,3-oxazolidine-5-carboxylate is obtained by carrying out the reaction as in Example 6 from appropriate starting materials and has the following characteristics:

N.M.R. spectrum: (400 MHz, CDCl₃, δ in ppm): 0.59 (q, J=7.5 Hz, 6H, —CH₂— ethyl, 0.93 (t, J=7.5 Hz, 9H, —CH₃ ethyl), 1.07 (s, 9H, —C(CH₃)₃), 1.17 (s, 3H, —CH₃ 16 or 17), 1.19 (s, 3H, —CH₃ 16 or 17), 1.64 (s, 6H, —CH₃ 19 and —CH₃ 18), 1.83 (mt, 1H, >(CH) —H 6), 1.90 (s, 3H, —COCH₃), 2.07 and 2.18 (2 dd, J=16 and 9 Hz, each 1H, —CH₂— 14), 2.49 (mt, 1H, >(CH) —H 6), 3.52 (s, 3H, —OCH₃), 3.72 (d, J=7 Hz, 1H, —H 3), 3.82 (s, 3H, Ar—OCH₃), 4.06 (d, J=8.5 Hz, 1H, >(CH) —H 20), 4.16 (limit AB, J=16 Hz, 2H, —OCOCH₂O—), 4.16 (d, J=8.5 Hz, 1H, >(CH) —H 20), 4.41 (dd, J=11 and 7 Hz, 1H, —H 7), 4.58 (d, J=6 Hz, 1H, —H 2'), 4.86 (broad d, J=10 Hz, 1H, —H 5), 5.43 (unresolved peak, 1H, —H 3'), 5.61 (d, J=7 Hz, 1H, —H 2), 6.03 (broad t, J =9 Hz, 1H, —H 13), 6.40 (unresolved peak, 1H, —H 5'), 6.43 (s, 1H, —H 10), 6.92 (d, J=8.5 Hz, 2H, —C₆H₅ at 5'(—H 3 and —H 5)), 7.41 (d, J=8.5 Hz, 2H, —C₆H₅ at 5'(—H 2 and H 6)), 7.42 (mt, 5H, —C₆H₅ at 3'), 8.18 (d, J =8.5 Hz, 2H, aromatic —H meta to —NO₂), 8.32 (d, J=8.5 Hz, 2H, aromatic —H ortho to —NO₂).

4α-Acetoxy-1β,7β-dihydroxy-5β,20-epoxy-2α-(4-nitrobenzoyloxy) -10β-methoxyacetoxy-9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl₃, δ in ppm): 1.15 (s, 3H, —CH₃ 16 or 17), 1.25 (s, 3H, —CH₃ 16 or 17), 1.35 (s, 9 H, —(CH₃)₃), 1.67 (s, 1H, —OH at 1), 1.78 (s, 3H, —CH₃ 19), 1.87 (mt, 1H, >(CH) —H 6), 1.90 (s, 3H, —CH₃ 18), 2.28 and 2.34 (2 dd, J=16 and 9 Hz, each 1H —CH₂— 14), 2.30 (d, J=2 Hz, 1H, —OH at 7), 2.43 (s, 3H, —COCH₃), 2.62 [mt, 1H, >(CH) —H 6], 3.32 (unresolved peak, 1H, —OH at 2'), 3.96 (d, J=7 Hz, 1H, —H 3), 4.20 (d, J=8.5 Hz, 1H, >(CH) —H 20), 4.23 (broad s, 1H, —OH at 10), 4.25 (mt, 1H, —H 7), 4.26 (d, J=8.5 Hz, 1H, >(CH) —H 20), 4.68 (mt, 1H, —H 2'), 4.96 (broad d, J=10 Hz, 1H, —H 5), 5.22 (broad s, 1H, —H 10), 5.31 (broad d, J=10 Hz, 1H, —H 3'), 5.41 (d, J=10 Hz, 1H, —CONH—), 5.69 (d, J=7 Hz, 1H, —H 2), 6.27 (t, J=9 Hz, 1H, —H 13), from 7.30 to 7.50 (mt, 5H, —C₆H₅ at 3'), 8.30 (d, J=8.5 Hz, 2H, aromatic —H meta to —NO₂), 8.38 (d, J=8.5 Hz, 2H, aromatic —H ortho to —NO₂).

EXAMPLE 17

4α-Acetoxy-5β,20-epoxy-2α-(4-nitrobenzoyloxy)-9-oxo- 1β,7β,10β-trihydroxy-11-taxen-13α-yl (2R, 3S)-3-tert-butoxycarbonylamino-2-hydroxy-3-phenylpropionate is obtained by carrying out the reaction as in Example 7 and has the following characteristics:

N.M.R. spectrum: (400 MHz, CDCl₃, δ in ppm): 1.15 (s, 3H, —CH 16 or 17), 1.25 (s, 3H, —CH₃ 16 or 17), 1.35 (s, 9 H, —(CH₃)₃), 1.67 (s, 1H, —OH at 1), 1.78 (s, 3H, —CH₃ 19), 1.87 (mt, 1H, >(CH) —H 6), 1.90 (s, 3H, —CH₃ 18), 2.28 and 2.34 (2 dd, J=16 and 9 Hz, each 1H, —CH₃— 14), 2.30 (d, J=2 Hz, 1H, —OH at 7), 2.43 (s, 3H, —COCH₃), 2.62 (mt, 1H, >(CH) —H 6), 3.32 (unresolved peak, 1H, —OH at 2'), 3.96 (d, J=7 Hz, 1H, —H 3), 4.20 (d, J=8.5 Hz, 1H, >(CH) —H 20), 4.23 (broad s, 1H, —OH at 10), 4.25 (mt, 1H, —H 7), 4.26 (d, J=8.5 Hz, 1H, >CH) —H 20), 4.68 (mt, 1 H, —H 2'), 4.96 (broad d, J=10 Hz, 1H, H 5), 5.22 (broad s, 1H, —H 10), 5.31 (broad d, J=10 Hz, 1H, —H 3'), 5.41 (d, J=10 Hz, 1H, —CONH—), 5.69 (d, J=7 Hz, 1H, —H 2); 6.27 (t, J=9 Hz, 1H, —H 13), from 7.30 to 7.50 (mt, 5H, —C₆H₅ at 3'), 8.30 (d, J=8.5 Hz, 2H, aromatic —H meta to —NO₂), 8.38 (d, J=8.5 Hz, 2H, aromatic —H ortho to —NO₂).

EXAMPLE 18

4α-Acetoxy-5β,20-epoxy-2α-(4-ethylbenzoyloxy)-1β-hydroxy-10β-methoxyacetoxy-9-oxo-7β-triethylsilyloxy-11-taxen-13α-yl (2R, 4S,5R)-3-tertbutoxycarbonyl-2-(4-methoxyphenyl)-4-phenyl-1,3-oxazolidine-5-carboxylate is obtained by carrying out the reaction as in Example 6 from appropriate starting materials and has the following characteristics:

N.M.R. spectrum: (400 MHz, CDCl₃, δ in ppm): 0.58 (q, J=7.5 Hz, 6H, —CH₂— ethyl), 0.93 (t, J=7.5 Hz, 9H, —CH₃ ethyl), 1.07 (s, 9H, —C(CH₃)₃), 1.17 (s, 3H, —CH₃ 16 or 17), 1.19 (s, 3H, —CH₃ 16 or 17), 1.29 (t, J=7.5 Hz, 3H, Ar—CH₂—CH₃), 1.65 (s, 3H, —CH₃ 19), 1.67 (s, 3H, —CH₃ 18), 1.70 (s, 1H, —OH at 1), 1.83 (mt, 1H, >(CH) —H 6), 1.84 (s, 3H, —COCH₃), 2.09 and 2.18 (2 dd, J =16 and 9 Hz, each 1H, —CH₂— 14), 2.48 (mt, 1H, >(CH) —H 6), 2.74 (t, J=7.5 Hz, 2H, Ar—CH₂— ethyl), 3.51 (s, 3H, —OCH₃), 3.70 (d, J=7 Hz, 1H, —H 3), 3.82 (s, 3H, Ar—OCH₃), 4.09 (d, J=8 Hz, 1H, >(CH) —H 20), 4.17 (limit AB, J=16 Hz, 2H, —OCOCH₂O—), 4.25 (d, J=8 Hz, 1H, >(CH) —H 20), 4.42 (dd, J=11 and 7 Hz, 1H, —H 7), 4.57 (d, J=5 Hz, 1H, —H 2'), 4.86 (broad d, J =10 Hz, 1H, —H 5), 5.41 (unresolved peak, 1H, —H 3'), 5.61 (d, J=7 Hz, 1H, —H 2), 6.06 (broad t, J=9 Hz, 1H, —H 13), 6.39 (unresolved peak, 1H, —H 5'), 6.44 (s, 1H, —H 10), 6.92 (d, J=8.5 Hz, 2H, —C₆H₅ at 5' (—H 3 and —H 5)), 7.30 (d, J=8 Hz, 2H, aromatic —H ortho to ethyl, 7.40 (d, J=8.5 Hz, 2H, —C₆H₅ at 5' (—H 2 and —H 6)), 7.41 (mt, 5H, —C₆H5 at 3'), 7.95 (d, J=8 Hz, 2H, aromatic —H meta to ethyl).

4α-Acetoxy-1β,7β-dihydroxy-5β,20-epoxy-2α-(4-ethylbenzoyloxy)- 10β-methoxyacetoxy-9 -oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl₃, δ in ppm): 1.16 (s, 3H, —CH₃ 16 or 17), 1.26 (s, 3H, —CH₃ 16 or 17), 1.28 (t, J=7.5 Hz, 3H, —CH₃ ethyl), 1.35 (s, 9H, —C(CH₃)₃), 1.70 (s, 3H, —CH₃ 19), 1.76 (s, 1H, —OH at 1), 1.88 (s, 3H, —CH₃ 18), 1.90 (mt, 1H, >(CH) —H 6), 2.30 (limit AB, J=16 and 9 Hz, 2H, —CH₂— 14), 2.38 (d, J=4 Hz, 1H, OH at 7), 2.41 (s, 3H, CO—CH₃), 2.58 (mt, 1H, >(CH) —H 6), 2.74 (q, J=7.5 Hz, 2H, ArCH₂— ethyl), 3.35 (d, J=4 Hz, 1H, —OH at 2'), 3.53 (s, 3H, —OCH₃), 3.80 (d, J=7 Hz, 1H, —H 3 ), 4.18 (d, J=8.5 Hz, 1H, >(CH) —H 20), 4.26 (limit AB, J=16 Hz, 2H, —OCOCH₂O—), 4.34 (d, J=8.5 Hz, 1H, >(CH) —H 20), 4.43 (mt, 1 H, —H 7), 4.64 (mt, 1H, —H 2'), 4.96 (broad d, J=10 Hz, 1H, —H 5), 5.27 (broad d, J=10 Hz, 1H, —H 3'), 5.39 (d, J=10 Hz, 1H, —CONH—), 5.67 (d, J=7 Hz, 1H, —H 2), 6.24 (t, J=9 Hz, 1H, —H 13), 6.40 (s, 1H, —H 10), 7.34 (d, J=8 Hz, 2H, aromatic—H ortho to ethyl), from 7.30 to 7.45 (mt, 5H, —C₆H₅ at 3'), 8.03 (d, J=8 Hz, 2H, aromatic —H meta to ethyl).

EXAMPLE 19

4α-Acetoxy-5β,20-epoxy-2α-(4-ethylbenzoyloxy)-9-oxo- 1β,7β,10β-trihydroxy-11-taxen-13α-yl (2R, 3S )-3-tert-butoxycarbonylamino-2-hydroxy-3-phenylpropionate is obtained by carrying out the reaction as in Example 7 and has the following characteristics:

N.M.R. spectrum: (400 MHz, CDCl$_3$, δ in ppm): 1.14 (s, 3H, —CH$_3$ 16 or 17), 1.26 (s, 3H, —CH$_3$ 16 or 17), 1.28 (t, J=7.5 Hz, 3H, —CH$_3$ ethyl), 1.38 (s, 9 H, —C(CH$_3$)$_3$), 1.70 (s, 1H, —OH at 1), 1.78 (s, 3H, —CH$_3$ 19), 1.85 (mt, 1H, >(CH) —H 6), 1.86 (s, 3H, —CH$_3$ 18), 2.28 (limit AB, J=16 and 9 Hz, 2H, —CH$_2$— 14), 2.38 (s, 3H, —COCH$_3$), 2.60 (mt, 1H, >(CH) —H 6), 2.73 (q, J=7.5 Hz, 2H, ArCH$_2$— ethyl), 3.35 (unresolved peak, 1H, —OH at 2'), 3.91 (d, J=7 Hz, 1H, —H 3), 4.20 (d, J=8.5 Hz, 1H, >(CH) —H 20), 4.23 (broad s, 1H, —OH at 10), 4.25 (mt, 1H, —H 7), 4.34 (d, J=8.5 Hz, 1H, >(CH) —H 20), 4.64 (mt, 1H, —H 2'), 4.96 (broad d, J=10 Hz, 1H, —H 5), 5.21 (broad s, 1H, —H 10), 5.27 (broad d, J=10 Hz, 1H, —H 3'), 5.45 (d, J=10 Hz, 1H, —CONH—), 5.67 (d, J=7 Hz, 1H, —H 2), 6.22 (t, J=9 Hz, 1H, —H 13), 7.33 (d, J=8.5 Hz, 2H, aromatic —H ortho to ethyl), from 7.30 to 7.45 (mt, 5H, —C$_6$H$_5$ at 3'), 8.03 (d, J=8.5 Hz, 2H, aromatic —H meta to ethyl).

EXAMPLE 20

4α-Acetoxy-5β,20-epoxy-2α-pentafluorobenzoyloxy-1β-hydroxy- 10β-methoxyacetoxy-9-oxo-7β-triethylsilyloxy-11-taxen-13α-yl (2R, 4S, 5R)-3tert-butoxycarbonyl-2-(4-methoxyphenyl)-4-phenyl-1,3-oxazolidine-5-carboxylate is obtained by carrying out the reaction as in Example 6 from appropriate starting materials and has the following characteristics:

N.M.R. spectrum: (400 MHz, CDCl$_3$, δ in ppm): 0.57 (q, J=8 Hz, 6H, —CH$_2$— ethyl), 0.92 (t, J=8 Hz, 9H, —CH$_3$ ethyl), 1.07 (s, 9H, —C(CH$_3$)), 1.16 (s, 3H, —CH$_3$ 16 or 17), 1.19 (s, 3H, —CH$_3$ 16 or 17), 1.54 (s, 1H, —OH at 1), 1.67 (s, 9H, —CH$_3$ 19, —CH$_3$ 18 and —COCH$_3$), 1.86 (mt, 1H, >(CH) —H 6), 2.05 and 2.19 (2 dd, J=16 and 9 Hz, each 1H, —CH$_2$—14), 2.48 (mt, 1H, >CH) —H 6), 3.52 (s, 3H, —OCH$_3$), 3.68 (d, J=7 Hz, 1H, —H 3), 3.82 (s, 3H, Ar—OCH$_3$), 4.16 (limit AB, J=16 Hz, 2H, —OCOCH$_2$—), 4.18 (limit AB, J=8 Hz, 2H, —CH$_2$— 20), 4.38 (dd, J=11 and 6.5 Hz, 1H, —H 7), 4.56 (d, J=5.5 Hz, 1H, —H 2'), 4.82 (broad d, J=10 Hz, 1H, —H 5), 5.40 (unresolved peak, 1H, —H 3'), 5.62 (d, J=7 Hz, 1H, —H 2), 6.07 (broad t, J=9 Hz, 1H, —H 13), 6.37 (unresolved peak, 1H, —H 5'), 6.43 (s, 1H, —H 10), 6.92 (d, J=8.5 Hz, 2H, —C$_6$H$_5$ at 5' (—H 3 and —H 5)), from 7.35 to 7.45 (mt, 7H, —C$_6$H$_5$ at 3' and —C$_6$H$_5$ at 5' (—H 2 and —H 6)).

4α-Acetoxy-1β,7β-dihydroxy-5β,20-epoxy-2α-pentafluorobenzoyloxy-10β-methoxyacetoxy- 9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl$_3$, δ in ppm): 1.14 (s, 3H, —CH$_3$ 16 or 17), 1.27 (s, 3H, —CH$_3$ 16 or 17), 1.42 (s, 9 H, —C(CH$_3$)$_3$), 1.68 (s, 1H, —OH at 1), 1.72 (s, 3H, —CH$_3$ 19), 1.85 (s, 3H, —CH$_3$ 18), 1.91 (mt, 1H, >(CH) —H 6), 2.20 (s, 3H, —COCH$_3$), 2.23 and 2.35 (2 dd, J=16 and 9 Hz, each 1H, —CH$_2$— 14), 2.38 (d, J=4 Hz, 1H, —OH at 7), 2.57 (mt, 1H, >(CH)—H 6), 3.39 (d, J=4 Hz, 1H, —OH at 2'), 3.53 (s, 3H, —OCH$_3$), 3.78 (d, J=7 Hz, 1H, —H 3), 4.27 (limit AB, J=16 Hz, 2H, —OCOCH$_2$—), 4.30 (limit AB, J=8.5 Hz, 2H, —CH$_2$—20), 4.39 (mt, 1H, —H 7), 4.57 (mt, 1H, —H 2'), 4.94 (broad d, J=10 Hz, 1H, —H 5), 5.19 (broad d, J=10 Hz, 1H, —H 3'), 5.35 (d, J=10 Hz, 1H, —CONH—), 5.68 (d, J=7 Hz, 1H, —H 2), 6.16 (t, J=9 Hz, 1H, —H 13), 6.38 (s, 1H, —H 10), from 7.30 to 7.45 (mt, 5H, —C$_6$H$_5$ at 3').

EXAMPLE 21

4α-Acetoxy-5β,20-epoxy-2α-pentafluorobenzoyloxy-9-oxo- 1β,7β,10β-trihydroxy-11-taxen-13α-yl (2R,3S)-3-tert-butoxycarbonylamino-2-hydroxy-3-phenylpropionate is obtained by carrying out the reaction as in Example 7 and has the following characteristics:

N.M.R. spectrum: (400 MHz, CDCl$_3$, δ in ppm): 1.12 (s, 3H, —CH$_3$ 16 or 17), 1.26 (s, 3H, —CH$_3$ 16 or 17), 1.43 (s, 9 H, —C(CH$_3$)$_3$), 1.68 (d, J=12.5 Hz, 1H, —OH at 7), 1.78 (s, 3H, —CH$_3$ 19), from 1.75 to 1.90 (mt, 1H, >(CH) —H 6), 1.83 (s, 3H, —CH$_3$ 18), 2.19 (s, 3H, —COCH$_3$), 2.20 and 2.29 (2 dd, J=16 and 9 Hz, each 1H, —CH$_2$—14), 2.58 (mt, 1H, >CH) —H 6), 3.88 (d, J=7 Hz, 1H, —H 3), from 4.15 to 4.30) (unresolved peak, 1H, —OH at 10), 4.22 (mt, 1H, —H 7), 4.30 (limit AB, J=8.5 Hz, 2H, —CH$_2$— 20), 4.55 (mt, 1H, —H 2'), 4.93 (broad d, J=10 Hz, 1H, —H 5), 5.19 (broad d, J=10 Hz, 1H, —H 3'), 5.20 (broad s, 1H, —H 10), 5.45 (d, J=10 Hz, 1H, —CONH—), 5.68 (d, J=7 Hz, 1H, —H 2), 6.15 (t, J=9 Hz, 1H, —H 13), from 7.30 to 7.45 (mt, 5H, —C$_6$H$_5$ at 3').

EXAMPLE 22

2α,4α-Diacetoxy-5β,20-epoxy-1β-hydroxy-10β-methoxyacetoxy-9-oxo- 7β-triethylsilyloxy-11-taxen-13α-yl (2R,4S,5R)-3-tert-butoxycarbonyl-2-(4-methoxyphenyl )-4-phenyl-1,3 -oxazolidine- 5-carboxylate is obtained by carrying out the reaction as in Example 6 from appropriate starting materials and has the following characteristics:

N.M.R. spectrum: (400 MHz, CDCl$_3$, δ in ppm): 0.59 (q, J=7.5 Hz, 6H, —CH$_2$— ethyl), 0.92 (t, J=7.5 Hz, 9H, —CH$_3$ ethyl), 1.09 (s, 9H, —C(CH$_3$)$_3$), 1.14 (s, 3H, —CH$_3$ 16 or 17), 1.16 (s, 3H, —CH$_3$ 16 or 17), 1.58 (s, 1H, —OH at 1), 1.60 (s, 3H, —CH$_3$ 19), 1.66 (s, 3H, —CH$_3$ 18), 1.82 (s, 3H, —COCH$_3$ at 4), 1.85 (mt, 1H, >(CH) —H 6), 1.95 (dd, J=16 and 9 Hz, 1H, >(CH) —H 14), 2.03 (s, 3H, —COCH$_3$ at 2), 2.18 (dd, J=16 and 9 Hz, 1H, >(CH) —H 14), 2.47 (mt, 1H, >(CH) —H 6), 3.51 (s, 3H, —OCH$_3$), 3.60 (d, J=7 Hz, 1H, —H 3), 3.81 (s, 3H, Ar—OCH$_3$), 4.13 (limit AB, J=16 Hz, 2H, —OCOCH$_2$O—), 4.15 (d, J=8 Hz, 1H, >(CH) —H 20), 4.40 (d, J=8 Hz, 1H, >(CH) —H 20), 4.40 (mt, 1H, —H 7), 4.53 (d, J=5 Hz, 1H, —H 2'), 4.86 (broad d, J=10 Hz, 1H, —H 5), 5.35 (d, J=7 Hz, 1H, —H 2), 5.46 (d, J=5 Hz, 1H, —H 3'), 5.99 (t, J=9 Hz, 1H, —H 13), 6.37 (s, 1H, —H 5'), 6.40 (s, 1H, —H 10), 6.92 (d, J=8.5 Hz, 2H, —C$_6$H$_5$ at 5' (—H 3 and —H 5)), from 7.30 to 7.50 (mt, 5H, —C$_6$H5 at 3'), 7.40 (d, J=8.5 Hz, 2H, —C$_6$H$_5$ at 5' (—H 2 and —H 6)).

2α,4α-Diacetoxy-1β,7β-dihydroxy-5β,20-epoxy- 10β-methoxyacetoxy-9-oxo-11-taxen-13α-yl (2R, 3S)-3-tert-butoxycarbonylamino-2-hydroxy-3-phenylpropionate is obtained by carrying out the reaction as in Example 6 and has the following characteristics:

N.M.R. spectrum: (400 MHz, CDCl$_3$, δ in ppm): 1.10 (s, 3H, —CH$_3$ 16 or 17), 1.24 (s, 3H, —CH$_3$ 16 or 17), 1.43 (s, 9H, —C(CH$_3$)$_3$), 1.65 (s, 3H, —CH$_3$ 19), 1.85 (s, 3H, —CH$_3$ 18), 1.90 (mt, 1H, >(CH)—H 6), 2.13 (s, 3H, —COCH$_3$ at 2), 2.23 (mt, 1H, >(CH) —H 14), 2.26 (s, 3H, —COCH$_3$), 2.36 (mt, 2H, —OH at 7 and >(CH) —H 14), 2.58 (mt, 1H, >(CH) —H 6), 3.32 (d, J=5.5 Hz, 1H, OH at 2'), 3.53 (s, 3H, —OCH$_3$), 3.90 (d, J=7 Hz, 1H, —H 3), 4.22 (d, J=8.5 Hz, 1H, >(CH) —H 20), 4.25 (limit AB, J=16 Hz, 2H, —OCOCH$_2$O—), 4.39 (mt, 1H, —H 7), 4.50 (d, J=8.5 Hz, 1H, >(CH) —H 20), 4.57 (dd, J=5.5 and 2 Hz, 1H, —H 2'), 4.96 (broad d, J=10 Hz, 1H, —H 5), 5.20 (broad d, J=10 Hz, 1H, —H 3'), 5.37 (d, J=10 Hz, 1H, —CONH—), 5.41 (d, J=7 Hz, 1H, —H 2), 6.15 (t, J=9 Hz, 1H, —H 13), 6.37 (s, 1H, —H 10), from 7.30 to 7.45 (mt, 5H, —C$_6$H$_5$ at 3').

EXAMPLE 23

2α,4α-Diacetoxy-1β,7β,10β-trihydroxy-5β,20-epoxy-9-oxo-11-taxen-13α-yl (2R, 3S)-3-tert-butoxycarbonylamino-2-hydroxy-3-phenylpropionate is obtained by carrying out the reaction as in Example 7 and has the following characteristics:

N.M.R. spectrum: (400 MHz, CDCl$_3$, δ in ppm): 0.59 (q, J=7.5 Hz, 6H, —CH$_2$-ethyl), 0.92 (t, J=7.5 Hz, 9H, —CH$_3$ ethyl), 1.09 (s, 9H, —C(CH$_3$)$_3$), 1.14 (s, 3H, —CH$_3$ 16 or 17), 1.16 (s, 3H, —CH$_3$ 16 or 17), 1.58 (s, 1H, —OH at 1), 1.60 (s, 3H, —CH$_3$ 19), 1.66 (s, 3H, —CH$_3$ 18), 1.82 (s, 3H, —COCH$_3$ at 4), 1.85 (mt, 1H, >(CH) —H 6), 1.95 (dd, J=16 and 9 Hz, 1H, >(CH) —H 14), 2.03 (s, 3H, —COCH$_3$ at 2), 2.18 (dd, J=16 and 9 Hz, 1H, >(CH) —H 14), 2.47 (mt, 1H, >(CH) —H 6), 3.51 (s, 3H, —OCH$_3$), 3.60 (d, J=7 Hz, 1H, —H 3), 3.81 (s, 3H, Ar—OCH$_3$), 4.13 (limit AB, J=16 Hz, 2H, —OCOCH$_2$O—), 4.15 (d, J=8 Hz, 1H, >(CH) —H 20), 4.40 (d, J=8 Hz, 1H, >(CH) —H 20), 4.40 (mt, 1H, —H 7), 4.53 (d, J=5 Hz, 1H, —H 2'), 4.86 (broad d, J=10 Hz, 1H, —H 5), 5.35 (d, J =7 Hz, 1H, —H 2), 5.46 (d, J=5 Hz, 1H, —H 3'), 5.99 (t, J=9 Hz, 1H, —H 13), 6.37 (s, 1H, —H 5'), 6.40 (s, 1H, —H 10), 6.92 (d, J=8.5 Hz, 2H, —C$_6$H$_5$ at 5'(—H 3 and —H 5)), from 7.30 to 7.50 (mt, 5H, —C$_6$H$_5$ at 3'), 7.40 (d, J=8.5 Hz, 2H, —C$_6$H$_5$ at 5' (—H 2 and —H 6)).

The new products of general formula (I) manifest significant inhibitory activity with respect to abnormal cell proliferation, and possess therapeutic properties that enable patients having pathological conditions associated with an abnormal cell proliferation to be treated. The pathological conditions include the abnormal cell proliferation of malignant or nonmalignant cells of various tissues and/or organs comprising, without implied limitation, muscle, bone or connective tissue, the skin, brain, lungs, sex organs, lymphatic or renal systems, mammary or blood cells, liver, digestive system, pancreas and thyroid or adrenal glands. These pathological conditions can also include psoriasis, solid tumors, cancers of the ovary, breast, brain, prostate, colon, stomach, kidney or testicles, Kaposi's sarcoma, cholangiocarcinoma, choriocarcinoma, neuroblastoma, Wilms' tumor, Hodgkin's disease, melanomas, multiple myeloma, chronic lymphocytic leukaemia, and acute or chronic granulocytic lymphoma. The new products according to the invention are especially useful for the treatment of cancer of the ovary. The products according to the invention may be used to prevent or delay the appearance or reappearance of the pathological conditions, or for treating these pathological conditions.

The products according to the invention may be administered to a patient according to different forms suited to the chosen administration route, which is preferably the parenteral route. Parenteral administration comprises intravenous, intraperitoneal, intramuscular or subcutaneous administrations. Intraperitoneal or intravenous administration is more especially preferred.

The present invention also comprises pharmaceutical compositions containing at least one product of general formula (I) in a sufficient amount suitable for use in human or veterinary therapy. The compositions may be prepared according to the customary methods, using one or more pharmaceutically acceptable adjuvants, vehicles or excipients. Appropriate vehicles include diluents, sterile aqueous media and various nontoxic solvents. Preferably, the compositions take the form of aqueous solutions or suspensions, injectable solutions which can contain emulsifying agents, colorants, preservatives or stabilizers.

The choice of adjuvants or excipients may be determined by the solubility and chemical properties of the product, the particular mode of administration and good pharmaceutical practice.

For parenteral administration, sterile aqueous or nonaqueous solutions or suspensions are used. For the preparation of nonaqueous solutions or suspensions, natural vegetable oils such as olive oil or sesame oil or liquid paraffin or injectable organic esters such as ethyl oleate may be used. The sterile aqueous solutions can consist of a solution of a pharmaceutically acceptable salt dissolved in water. Aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is obvious that all the products participating in the compositions according to the invention must be pure and nontoxic in the amounts used.

The compositions can contain at least 0.01% of therapeutically active product. The amount of active product in a composition is such as to enable an appropriate dosage to be prescribed. Preferably, the compositions are prepared in such a way that a single dose contains from 0.01 to 1,000 mg approximately of active product for parenteral administration.

The therapeutic treatment may be carried out conjointly with other therapeutic treatments including antineoplastic medicinal products, monoclonal antibodies, immunological therapies or radiotherapies or biological-response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents such as nitrogen mustards, for instance mechlorethamine, cyclophosphamide, melphalan and chlorambucil, alkyl sulphonates such as busulphan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products such as vinca alkaloids, for instance vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for example cisplatin, substituted ureas such as hydroxyurea, methylhydrazine derivatives such as procarbazine, adrenocorticoid suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethinyloestradiol, antioestrogens such as tamoxifen, and androgens such as testosterone propionate and fluoxymesterone.

The doses used for implementing the methods according to the invention are those which permit a prophylactic treatment or a maximum therapeutic response. The doses vary according to the form of administration, the particular product selected and the features distinctive to the subject to be treated. In general, the doses are those which are therapeutically effective for the treatment of disorders due to an abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly higher doses will be administered until an optimum effect is obtained. For other patients, it may be necessary to administer maintenance doses 1 to 8 times daily, preferably 1 to 4 times, according to the physiological requirements of the patient in question. For some patients, it is also possible for it to be necessary to use only one to two daily administrations.

In humans, the doses are generally between 0.01 and 200 mg/kg. Intraperitoneally, the doses will generally be between 0.1 and 100 mg/kg, and preferably between 0.5 and 50 mg/kg, and still more specifically between 1 and 10 mg/kg. Intravenously, the doses are generally between 0.1 and 50 mg/kg, and preferably between 0.1 and 5 mg/kg, and still more specifically between 1 and 2 mg/kg. It is understood that, in order to choose the most suitable dosage, account should be taken of the administration route, the patient's weight, general state of health and age and all factors which may influence the efficacy of the treatment.

The following example illustrates a composition according to the invention.

EXAMPLE 40 mg of the product obtained in Example 1 are dissolved in 1 cm$^3$ of Emulphor EL 620 and 1 cm$^3$ of ethanol and the solution is then diluted by addition of 18 cm$^3$ of physiological saline.

The composition is administered by perfusion for 1 hour by introduction in physiological solution.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Taxoids of formula I:

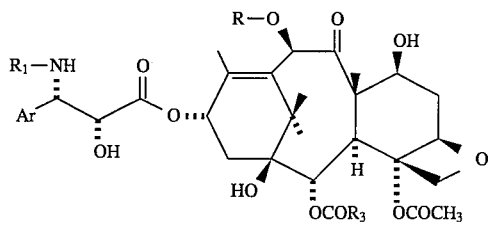

in which

Ar represents an aryl radical or a heterocylic radical,

R represents a hydrogen atom or an acetyl or alkoxyacetyl radical, $R_1$ represents a benzoyl radical or a radical $R_2$—O—CO— in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms, or a bicycloalkyl radical containing 7 to 11 carbons atoms, these radicals unsubstituted or substituted by at least one substituent selected from halogen atoms and hydroxyl radicals, alkyloxy radicals containing 1 to 4 carbon atoms, dialkylamino radicals in which each alkyl part contains 1 to 4 carbon atoms, piperidino radicals, morpholino radicals, 1-piperazinyl radicals (unsubstituted or substituted in the 4-position by an alkyl radical containing 1 to 4 carbon atoms or by a phenylalkyl radical in which the alkyl part contains 1 to 4 carbon atoms), cycloalkyl radicals containing 3 to 6 carbon atoms, cycloalkenyl radicals containing 4 to 6 carbon atoms, phenyl radicals, cyano radicals, caxboxyl radicals, or alkoxycarbonyl radicals in which the alkyl part contains 1 to 4 carbon atoms;

or by a phenyl radical unsubstituted or substituted by at least one atom or radical selected from halogen atoms, alkyl radicals containing 1 to 4 carbon atoms, or alkyloxy radicals containing 1 to 4 carbon atoms;

or by a saturated or unsaturated heterocyclyl radical containing 4 to 6 members and unsubstituted or substituted by at least one alkyl radical containing 1 to 4 carbon atoms; and $R_3$ represents:

a cycloalkyl radical containing 3 to 6 carbon atoms, a cycloalkenyl radical containing 4 to 6 carbon atoms, or a bicycloalkyl radical containing 7 to 11 carbons atoms, these radicals unsubstituted or substituted by at least one substituent selected from halogen atoms and hydroxyl radicals, alkyloxy radicals containing 1 to 4 carbon atoms, dialkylamino radicals in which each alkyl part contains 1 to 4 carbon atoms, piperidino radicals, morpholino radicals, 1-piperazinyl radicals (unsubstituted or substituted in the 4-position by an alkyl radical containing 1 to 4 carbon atoms or by a phenylalkyl radical in which the alkyl part contains 1 to 4 carbon atoms), cycloalkyl radicals containing 3 to 6 carbon atoms, cycloalkenyl radicals containing 4 to 6 carbon atoms, or phenyl radicals, unsubstituted or substituted by cyano radicals, carboxyl radicals, or alkoxycarbonyl radicals in which the alkyl part contains 1 to 4 carbon atoms;

wherein the cycloalkyl, cycloalkenyl, or bicycloalkyl radicals can be unsubstituted or substituted by at least one alkyl radical containing 1 to 4 carbon atoms.

2. Taxoids according to claim 1, wherein R and $R_1$ are defined as in claim 1, the aryl radicals represented by Ar are phenyl or α- or β-naphthyl radicals unsubstituted or substituted by at least one atom or radical selected from halogen atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms, the alkenyl and alkynyl radicals contain 2 to 8 carbon atoms, the aryl radicals are phenyl or α or β-naphthyl radicals, and the heterocyclic radicals represented by Ar are aromatic heterocyclic radicals having 5 members and containing at least one atom, which is identical or different, selected from nitrogen, oxygen or sulphur atoms, unsubstituted or substituted by at least one substituent, which is identical or different, selected from halogen atoms and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, alkylamino radicals in which the alkyl part contains 1 to 4 carbon atoms, acylamino radicals in which the acyl part contains 1 to 4 carbon atoms, alkoxycarbonylamino radicals containing 1 to 4 carbon atoms, acyl radicals containing 1 to 4 carbon atoms, arylcarbonyl radicals in which the aryl part contains 6 to 10 carbon atoms, cyano radicals, nitro trifluoromethyl radicals, carboxyl radicals, carbamoyl radicals, alkylcarbamoyl radicals in which the alkyl part contains 1 to 4 carbon atoms, dialkylcarbamoyl radicals in which each alkyl part contains 1 to 4 carbon atoms, or alkoxycarbonyl radicals in which the alkoxy part contains 1 to 4 carbon atoms.

3. Taxoids according to claim 1, wherein R and $R_1$ are defined as in claim 1, and Ar represents a phenyl, 2-or 3-thienyl, 2-or 3-furyl, or 2-, 4- or 5-thiazolyl radical, unsubstituted or substituted by at least one atom or radical, which is identical or different, selected from halogen atoms and alkyl, alkoxy, amino, alkylamino, dialkylamino, acylamino, alkoxycarbonylamino and trifluoromethyl radicals.

4. Taxoids according to claim 1, wherein R represents a hydrogen atom or an acetyl or methoxyacetyl radical, Ar represents a phenyl radical, and $R_1$ represents a benzoyl or tert-butoxylcarbonyl radical.

5. Pharmaceutical composition comprising an effective amount of at least one product according to claim 1, in combination with at least one pharmaceutically acceptable product optionally inert or physiologically active.

6. Taxoids according to claim 2, wherein the halogen atom is fluorine, chlorine, bromine, or iodine.

* * * * *